(12) United States Patent
Ehrnsperger et al.

(10) Patent No.: US 8,921,641 B2
(45) Date of Patent: Dec. 30, 2014

(54) ABSORBENT ARTICLE HAVING IMPROVED ABSORPTION PROPERTIES

(75) Inventors: Bruno Johannes Ehrnsperger, Bad Soden (DE); Marc Jennewein, Taunusstein (DE); Marion Michnacs, Schwalbach/Ts (DE); Andrea Peri, Schwalbach/Ts (DE); Maike Thomann, Kriftel (DE)

(73) Assignee: The Procter & Gamble Company, Cincinnati, OH (US)

( * ) Notice: Subject to any disclaimer, the term of this patent is extended or adjusted under 35 U.S.C. 154(b) by 253 days.

(21) Appl. No.: 13/524,006

(22) Filed: Jun. 15, 2012

(65) Prior Publication Data

US 2012/0323195 A1 Dec. 20, 2012

(30) Foreign Application Priority Data

Jun. 17, 2011 (EP) .................................. 11004976

(51) Int. Cl.
| A61F 13/15 | (2006.01) |
| A61F 13/49 | (2006.01) |
| A61F 13/513 | (2006.01) |
| A61F 13/53 | (2006.01) |
| A61F 13/534 | (2006.01) |
| A61F 13/535 | (2006.01) |
| A61F 13/532 | (2006.01) |

(52) U.S. Cl.
CPC . *A61F 13/15203* (2013.01); *A61F 2013/15544* (2013.01); *A61F 2013/15406* (2013.01); *A61F 13/535* (2013.01); *A61F 13/534* (2013.01); *A61F 13/15* (2013.01); *A61F 2013/15382* (2013.01); *A61F 2013/15463* (2013.01); *A61F 2013/15373* (2013.01); *A61F 13/53* (2013.01); *A61F 13/5323* (2013.01)

USPC ........... 604/367; 604/327; 604/358; 604/366; 604/370; 604/385.23; 502/402

(58) Field of Classification Search
CPC ... A61F 13/15; A61F 13/5323; A61F 13/534; A61F 13/535; A61F 13/15203; A61F 13/53; A61F 2013/15; A61F 2013/1513; A61F 2013/15146; A61F 2013/15373; A61F 2013/15382; A61F 2013/15406; A61F 2013/15414; A61F 2013/15463; A61F 2013/15471; A61F 2013/15479; A61F 2013/15512; A61F 2013/1552; A61F 2013/1556; A61F 13/0209; A61F 2013/00748; A61F 2013/428; A61F 2013/530306; A61F 2013/530481; A61F 2013/5307
See application file for complete search history.

(56) References Cited

U.S. PATENT DOCUMENTS

| 3,860,003 A | 1/1975 | Buell |
| 3,929,135 A | 12/1975 | Thompson |

(Continued)

FOREIGN PATENT DOCUMENTS

| EP | 149880 A2 | 7/1985 |
| WO | WO 95/16746 A1 | 6/1995 |
| WO | WO 99/34841 A1 | 7/1999 |

OTHER PUBLICATIONS

International Search Report, PCT/US2012/042112, mailed Oct. 18,2012, 11 pages.

*Primary Examiner* — Adam Marcetich
(74) *Attorney, Agent, or Firm* — Andrew J. Mueller; Andrew A Paul; Richard L. Alexander

(57) ABSTRACT

An absorbent article such as disposable diaper, training pant, and adult incontinence undergarment comprising superabsorbent polymer particles able to absorb and contain body exudates having improved absorption properties and, therefore, reduce leakage, especially at the first gush, i.e. when the article starts to be wetted.

16 Claims, 13 Drawing Sheets

(56) References Cited

U.S. PATENT DOCUMENTS

| | | | |
|---|---|---|---|
| 4,324,246 A | 4/1982 | Mullane et al. | |
| 4,340,706 A | 7/1982 | Obayashi et al. | |
| 4,342,314 A | 8/1982 | Radel et al. | |
| 4,463,045 A | 7/1984 | Ahr et al. | |
| 5,006,394 A | 4/1991 | Baird | |
| 5,149,335 A * | 9/1992 | Kellenberger et al. | 604/372 |
| 5,151,092 A | 9/1992 | Buell et al. | |
| 5,342,338 A | 8/1994 | Roe | |
| 5,431,643 A | 7/1995 | Ouellette et al. | |
| 5,571,096 A | 11/1996 | Dobrin et al. | |
| 5,849,816 A | 12/1998 | Suskind et al. | |
| 6,121,509 A | 9/2000 | Ashraf et al. | |
| 6,645,569 B2 | 11/2003 | Cramer et al. | |
| 6,863,933 B2 | 3/2005 | Cramer et al. | |
| 7,112,621 B2 | 9/2006 | Rohrbaugh et al. | |
| 7,537,832 B2 | 5/2009 | Carlucci et al. | |
| 8,236,715 B2 | 8/2012 | Schmidt et al. | |
| 2003/0014027 A1 * | 1/2003 | Beihoffer et al. | 604/368 |
| 2003/0105190 A1 | 6/2003 | Diehl et al. | |
| 2003/0148684 A1 | 8/2003 | Cramer et al. | |
| 2005/0008839 A1 | 1/2005 | Cramer et al. | |
| 2005/0070867 A1 * | 3/2005 | Beruda et al. | 604/367 |
| 2005/0101928 A1 * | 5/2005 | Beruda et al. | 604/367 |
| 2005/0159720 A1 | 7/2005 | Gentilcore et al. | |
| 2005/0222547 A1 * | 10/2005 | Beruda et al. | 604/368 |
| 2007/0156108 A1 * | 7/2007 | Becker et al. | 604/372 |
| 2008/0262459 A1 * | 10/2008 | Kamoto et al. | 604/375 |
| 2008/0269705 A1 * | 10/2008 | Kainth et al. | 604/367 |
| 2009/0192035 A1 | 7/2009 | Stueven et al. | |
| 2009/0258994 A1 | 10/2009 | Stueven et al. | |
| 2009/0270825 A1 | 10/2009 | Wciorka et al. | |
| 2010/0068520 A1 | 3/2010 | Stueven et al. | |
| 2010/0312212 A1 * | 12/2010 | Bond et al. | 604/378 |
| 2011/0313113 A1 | 12/2011 | Sakamoto et al. | |
| 2013/0079740 A1 * | 3/2013 | Ehrnsperger et al. | 604/370 |

* cited by examiner

ABSORBENT ARTICLE HAVING IMPROVED ABSORPTION PROPERTIES

FIELD

The present disclosure is directed to absorbent articles such as disposable diapers, training pants and adult incontinence undergarments comprising superabsorbent polymer particles.

BACKGROUND

Absorbent articles, such as disposable diapers, training pants, and adult incontinence undergarments, absorb and contain body exudates. Many absorbent articles, like diapers, contain superabsorbent polymer material. Superabsorbent polymers are typically present in the core of the absorbent articles in the form of particles. Superabsorbent polymer particles are able to absorb liquid and swell when entering into contact with liquid exudates. However, it has been shown in the past that not all categories of superabsorbent polymer particles are equally suitable for use in an absorbent article.

It is generally known that in order to have absorbent articles comprising superabsorbent polymer particles which exhibit good absorbing and containing functions, specific technical requirements should generally be fulfilled by the superabsorbent polymer particles.

The superabsorbent polymer particles should first to be able to absorb the liquid exudates fast. The absorption speed of superabsorbent polymer particles has generally been characterized in the prior art by measuring the Free Swell Rate (FSR) of the particles.

In addition to having a high absorption speed, the superabsorbent polymer particles present in the core should be also highly permeable to liquid. A poor permeability of the superabsorbent polymer particles may induce leakage of the absorbent article due to gel blocking Gel blocking can occur in the absorbent core when swelling superabsorbent polymer particles block the void spaces between the particles. In such a case, the liquid exudates can not or only slowly reach underneath layers of superabsorbent polymer particles disposed in the core. The liquid exudates remain on the surface of the absorbent core and may therefore leak from the diaper.

The permeability of the superabsorbent polymer particles has typically been characterized in the prior art by measuring the SFC (Saline Flow Conductivity) of the particles. This parameter is measured at equilibrium, i.e. the measure is performed on a fully preswollen gel bed of superabsorbent polymer particles.

However, the inventors have now surprisingly found that superabsorbent polymer particles having high FSR and high SFC values do not automatically conduct to fast acquisition times of liquid exudates into the absorbent article, especially at the first gush, i.e. when the dry superabsorbent polymer particles first come into contact with liquid.

The present disclosure therefore provides an absorbent article having improved absorption properties and, therefore, reduced leakage, especially at the first gush, i.e. when the article starts to be wetted.

SUMMARY

The present disclosure relates to an absorbent article comprising an absorbent core. The absorbent article is divided into three portions: a front portion, a back portion and a crotch portion disposed between the front portion and the back portion. The absorbent core has a dry thickness at the crotch point of the article of from 0.2 to 5 mm. The absorbent core comprises at least 90% of superabsorbent polymer particles. The superabsorbent polymer particles comprised by the absorbent core in the front portion or the crotch portion of the article or by the whole absorbent core require a time to reach an uptake of 20 g/g (T20) of less than 240 s as measured according to the K(t) Test Method.

DETAILED DESCRIPTION

Figure 1:
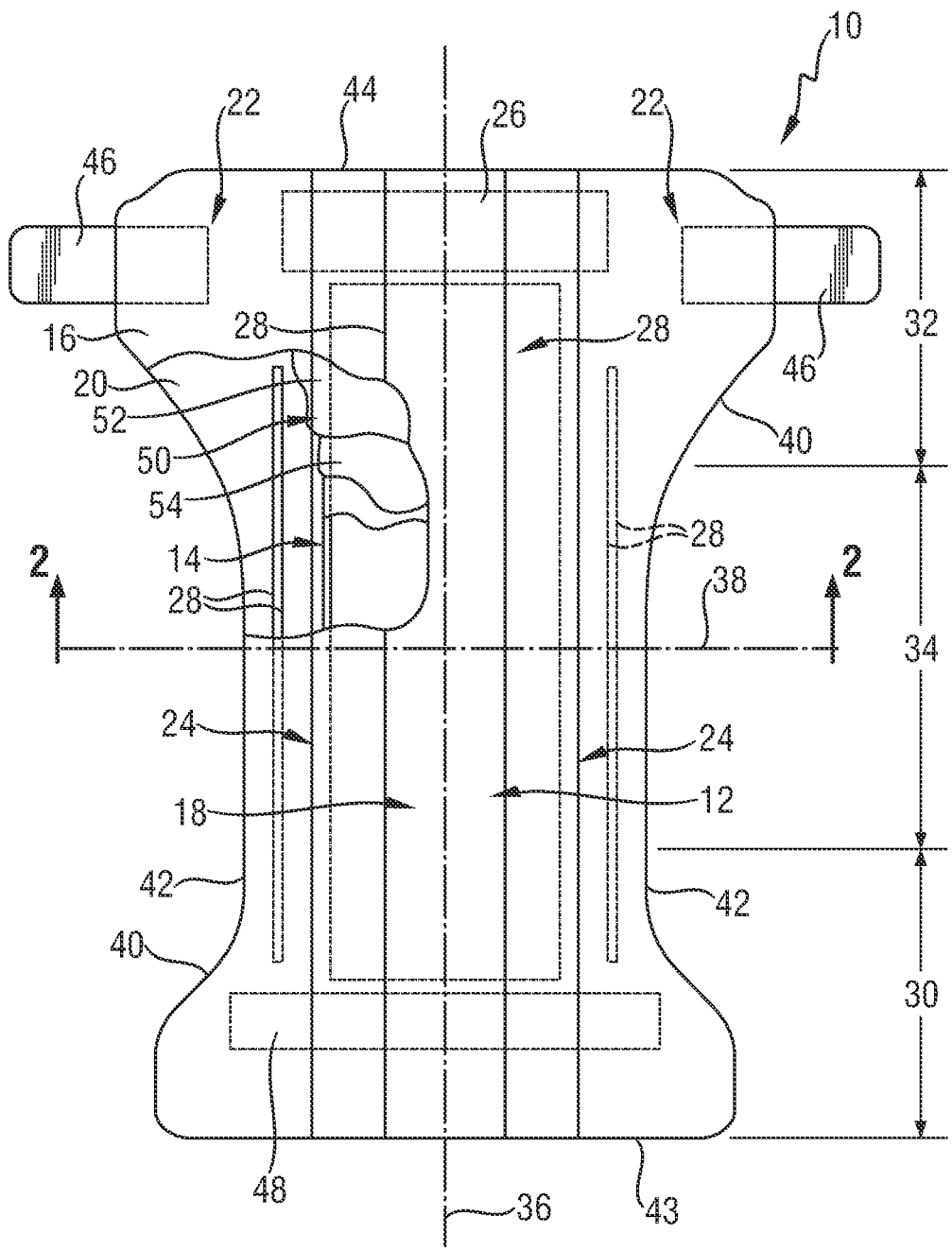
FIG. 1 is a plan view of a diaper in accordance with an embodiment of the present disclosure.

Absorbent article" is used herein to refer to devices that absorb and contain body exudates, and, more specifically, refers to devices that are placed against or in proximity to the body of the wearer to absorb and contain the various exudates discharged from the body. Absorbent articles include diapers, training pants, adult incontinence undergarments, feminine hygiene products and the like. As used herein, the term "body fluids" or "body exudates" includes, but is not limited to, urine, blood, vaginal discharges, breast milk, sweat and fecal matter. In some embodiments of the present disclosure, the absorbent article is a diaper or training pant.

"Absorbent core" is used herein to refer to a structure disposed between a topsheet and backsheet of an absorbent article for absorbing and containing liquid received by the absorbent article. This structure may comprise one or more substrate layer(s), superabsorbent polymer particles disposed on the one or more substrate layers, and a thermoplastic composition typically disposed on the superabsorbent polymer particles. Typically the thermoplastic composition is a thermoplastic adhesive material. In one embodiment, the thermoplastic adhesive material forms a fibrous layer which is at least partially in contact with the superabsorbent polymer particles on the one or more substrate layers and partially in contact with the one or more substrate layers. In one embodiment, auxiliary adhesive might be deposited on the one or more substrate layers before application of the superabsorbent polymer particles for enhancing adhesion of the superabsorbent polymer particles and/or of the thermoplastic adhesive material to the respective substrate layer(s). The absorbent core may also include one or more cover layer(s) such that the superabsorbent polymer particles are comprised between the one or more substrate layer(s) and the one or more cover layer(s). The one or more substrate layer(s) and the cover layer(s) may comprise or consist of a nonwoven. The absorbent core may further comprise odor control compounds.

In the embodiments wherein the absorbent article in addition to the absorbent core comprises a topsheet and/or a backsheet, and/or an acquisition system, the absorbent core does not include the topsheet, the backsheet and/or the acquisition system.

In some embodiments, the absorbent core consists essentially of the one or more substrate layer(s), the superabsorbent polymer particles, the thermoplastic composition, optionally the auxiliary adhesive, optionally the cover layer(s), and optionally odor control compounds.

"Crotch point" is used herein to refer to the point of the article which is positioned in the center of the absorbent article at the intersection of the longitudinal centerline and the transverse centerline of the article. It should be understood for the purpose of the present disclosure that the crotch point of the article is not necessarily positioned in the center of the absorbent core, namely at the intersection of the longitudinal centerline and the transverse centerline of the absorbent core, especially in case the absorbent core is not centered on the transverse centerline of the article, i.e. in case the absorbent core is shifted to the front and/or the back of the article.

"Airfelt" is used herein to refer to comminuted wood pulp, which is a form of cellulosic fiber.

"Superabsorbent polymer particle" is used herein to refer to cross linked polymeric materials that can absorb at least 10 times their weight of an aqueous 0.9% saline solution as measured using the Centrifuge Retention Capacity test (EDANA WSP 241.2-05). The superabsorbent polymer particles are in particulate form so as to be flowable in the dry state. Some superabsorbent polymer particles of the present disclosure are made of poly(meth)acrylic acid polymers. However, e.g. starch-based superabsorbent polymer particles are also comprised within the scope of the present disclosure "Thermoplastic adhesive material" is used herein to refer to a polymer composition from which fibers may be formed and applied to the superabsorbent polymer particles with the intent to immobilize the superabsorbent polymer particles in both the dry and wet state. The thermoplastic adhesive material of the present disclosure may form a fibrous network over the superabsorbent polymer particles.

"Front portion" and "back portion" is used herein to refer to the front and back waist regions of the absorbent article. The length of both the front portion and the back portion is one third of the overall length of the article starting at the respective front and back waist edges. For embodiments, wherein the front and/or back waist edge is/are not configured as a straight line extending in parallel to the transverse centerline of the absorbent article, the length of the absorbent article is determined on or parallel to the longitudinal centerline by starting from the point of the front waist edge which is closest to the transverse centerline and terminating at the point of back waist edge which is closest to the transverse centerline.

"Crotch portion" is used herein to refer to the region of the article positioned in the center of the article between the front and the back portion of the article. The length of the crotch portion is one third of the overall length of the article.

A "nonwoven" is used herein to refer to a manufactured sheet, web or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers have diameters ranging from less than about 0.001 mm to more than about 0.2 mm and they come in several different forms: short fibers (known as staple, or chopped), continuous single fibers (filaments or monofilaments), untwisted bundles of continuous filaments (tow), and twisted bundles of continuous filaments (yarn). Nonwoven fabrics can be formed by many processes such as meltblowing, spunbonding, solvent spinning, electrospinning, and carding. The basis weight of nonwoven fabrics is usually expressed in grams per square meter (gsm).

"Attached" is used herein to refer to configurations whereby a first element is directly secured to another element by affixing the first element directly to a second element or whereby a first element is indirectly secured to a second element by affixing the first element to a third, intermediate member(s), which in turn are affixed to the second element. The attachment means may comprise adhesive bonds, heat bonds, pressure bonds, ultrasonic bonds, dynamic mechanical bonds, or any other suitable attachment means or combinations of these attachment means as are known in the art.

FIG. 1 is a plan view of an absorbent article 10 according to some embodiments of the present disclosure. The absorbent article 10 is shown in its flat out, uncontracted state (i.e., without elastic induced contraction) and portions of the absorbent article 10 are cut away to more clearly show the underlying structure of the diaper 10. A portion of the absorbent article 10 that contacts a wearer is facing the viewer in FIG. 1. The absorbent article 10 generally comprises a chassis 12 and an absorbent core 14 disposed in the chassis 12.

The chassis 12 of the absorbent article 10 in FIG. 1 may comprise the main body of the absorbent article 10. The chassis 12 may comprise an outer covering 16 including a topsheet 18, which may be liquid pervious, and/or a backsheet 20, which may be liquid impervious. The absorbent core 14 may be encased between the topsheet 18 and the backsheet 20. The chassis 12 may also include side panels 22, elasticized leg cuffs 24, and an elastic waist feature 26.

The leg cuffs 24 and the elastic waist feature 26 may each typically comprise elastic members 28. One end portion of the absorbent article 10 is configured as the front portion 30 and the other end portion is configured as the back portion 32 of the absorbent article 10. The intermediate portion of the absorbent article 10 is configured as the crotch portion 34, which extends longitudinally between the front and back portions 30 and 32.

The absorbent article 10 is depicted in FIG. 1 with its longitudinal centerline 36 and its transverse centerline 38. The periphery 40 of the absorbent article 10 is defined by the outer edges of the absorbent article 10 in which the longitudinal edges 42 run generally parallel to the longitudinal centerline 36 of the absorbent article 10 and the front and back waist edges 43 and 44 run between the longitudinal edges 42 generally parallel to the transverse centerline 38 of the absorbent article 10. The chassis 12 may also comprise a fastening system, which may include at least one fastening member 46 and at least one landing zone 48.

The absorbent article 10 may also include such other features as are known in the art including front and rear ear panels, waist cap features, elastics and the like to provide better fit, containment and aesthetic characteristics. Such additional features are well known in the art and are e.g., described in U.S. Pat. No. 3,860,003 and U.S. Pat. No. 5,151,092.

In order to keep the absorbent article 10 in place about the wearer, at least a portion of the front portion 30 may be attached by the fastening member 46 to at least a portion of the back portion 32 to form leg opening(s) and an article waist. When fastened, the fastening system carries a tensile load around the article waist. The fastening system may allow an article user to hold one element of the fastening system, such as the fastening member 46, and connect the front portion 30 to the back portion 32 in at least two places. This may be achieved through manipulation of bond strengths between the fastening device elements.

According to certain embodiments, the absorbent article 10 may be provided with a re-closable fastening system or may alternatively be provided in the form of a pant-type diaper. When the absorbent article is a diaper, it may comprise a re-closable fastening system joined to the chassis for securing the diaper to a wearer. When the absorbent article is a pant-type diaper, the article may comprise at least two side panels joined to each other to form a pant.

The Absorbent Core

The absorbent core comprises at least 90% by weight of superabsorbent polymer particles based on the weight of the core, excluding the weight of any nonwoven web such as substrate layers and cover layers that might be comprised by the absorbent core.

In some embodiments, the absorbent core comprises at least 95% by weight of superabsorbent polymer particles.

In some embodiments, the absorbent core comprises at least 98% by weight of superabsorbent polymer particles.

In other embodiments, the absorbent core comprises at least 99% by weight of superabsorbent polymer particles.

These embodiments, in some instances, may be desired since absorbent articles comprising a high percentage of superabsorbent polymer particles typically have a reduced thickness when dry in comparison with the thickness of conventional absorbent articles having a higher amount of conventional absorbent materials, such as airfelt and the like in addition to the superabsorbent polymer particles. The reduced thickness helps to improve the fit and the comfort when the article is positioned on the wearer.

In some embodiments, the absorbent core comprises an average amount of superabsorbent polymer particles per area of from 50 to 2200 $g/m^2$ or 100 to 1500 $g/m^2$ or 200 to 1000 $g/m^2$.

In some embodiments, the absorbent core comprises an average amount of superabsorbent polymer particles per area of from 100 to 1500 $g/m^2$, or 150 to 1000 $g/m^2$, or 200 to 900 $g/m^2$, or 400 to 700 $g/m^2$ in the crotch portion of the article. The absorbent article comprises enough of an amount of superabsorbent polymer particles to have good absorption properties as well as to be sufficient thin to provide fit and comfort to the wearer. However, superabsorbent polymer particles are also present in the front and back portions, though especially in back portion amount may be low (or even zero). In some embodiments, the absorbent core comprises an average amount of superabsorbent polymer particles per surface area of less than 300 $g/m^2$, or less than 200 $g/m^2$, alternatively from 25 to 300 $g/m^2$, or 50 to 200 $g/m^2$ or 50 to 100 $g/m^2$ in the back portion of the article.

In some embodiments, the absorbent core may further comprise minor amounts of an absorbent material other than superabsorbent polymer particles, e.g. airfelt.

In some embodiments, the absorbent core typically comprises less than 5% by weight of airfelt, alternatively less than 2%, and alternatively is airfelt free.

The absorbent core has a dry thickness at the crotch point of the article of less than 10 mm, alternatively less than 5 mm, alternatively less than 3 mm, alternatively less than 1.5 mm, alternatively from 0.1 mm to 10 mm, alternatively from 0.2 mm to 5 mm, alternatively from 0.3 mm to 3 mm, and alternatively from 0.5 mm to 1.5 mm, as measured according to the Test Method set out below. The absorbent core is thus sufficiently thin compared to conventional airfelt containing absorbent cores. Thereby, fit and comfort is substantially improved.

The Superabsorbent Polymer Particles

The superabsorbent polymer particles useful for the present disclosure may be of numerous shapes. The term "particles" refers to granules, fibers, flakes, spheres, powders, platelets and other shapes and forms known to persons skilled in the art of superabsorbent polymer particles. In some embodiments, the superabsorbent polymer particles can be in the shape of fibers, i.e. elongated, acicular superabsorbent polymer particles. In those embodiments, the superabsorbent polymer particles fibers have a minor dimension (i.e. diameter of the fiber) of less than about 1 mm, usually less than about 500 µm, and alternatively less than 250 µm down to 50 µm. The length of the fibers may be about 3 mm to about 100 mm. The fibers can also be in the form of a long filament that can be woven.

Alternatively, in some embodiments, superabsorbent polymer particles of the present disclosure are spherical-like particles. According to the present disclosure and in contrast to fibers, "spherical-like particles" have a longest and a smallest dimension with a particulate ratio of longest to smallest particle dimension in the range of 1-5, where a value of 1 would equate a perfectly spherical particle and 5 would allow for some deviation from such a spherical particle. In such embodiments, the superabsorbent polymer particles may have a particle size of less than 850 µm, or from 50 to 850 µm, alternatively from 100 to 500 µm, and alternatively from 150 to 300 µm, as measured according to EDANA method WSP 220.2-05. Superabsorbent polymer particles having a relatively low particle size help to increase the surface area of the absorbent material which is in contact with liquid exudates and therefore support fast absorption of liquid exudates.

The superabsorbent polymer particles useful in the present disclosure include a variety of water-insoluble, but water-swellable polymers capable of absorbing large quantities of fluids. Such polymers materials are generally known in the art.

Suitable superabsorbent polymer particles may for example be obtained from inverse phase suspension polymerizations as described in U.S. Pat. No. 4,340,706 and U.S. Pat. No. 5,849,816 or from spray- or other gas-phase dispersion polymerizations as described in U.S. Patent Applications No. 2009/0192035, 2009/0258994 and 2010/0068520. In some embodiments, suitable superabsorbent polymer particles may be obtained by current state of the art production processes as is more particularly described from page 12, line 23 to page 20, line 27 of WO 2006/083584.

In some embodiments, the surface of the superabsorbent polymer particles may be coated. In such embodiments, the coating makes surface sticky so that superabsorbent polymer particles cannot rearrange (so they cannot block voids) easily upon wetting.

In some embodiments, the superabsorbent polymer particles may be coated with a cationic polymer. Some cationic polymers can include polyamine or polyimine materials which are reactive with at least one component included in body fluids, especially in urine. Some polyamine materials can be selected from the group consisting of (1) polymers having primary amine groups (e.g., polyvinylamine, polyallyl amine); (2) polymers having secondary amine groups (e.g., polyethyleneimine); and (3) polymers having tertiary amine groups (e.g., poly N,N-dimethylalkyl amine).

Practical examples of the cationic polymer are, for example, polyethyleneimine, a modified polyethyleneimine which is crosslinked by epihalohydrine in a range soluble in water, polyamine, a modified polyamidoamine by graft of ethyleneimine, polyetheramine, polyvinylamine, polyalkylamine, polyamidopolyamine, and polyallylamine.

In some embodiments, a cationic polymer has a weight-average molecular weight of at least 500, alternatively 5,000, and alternatively 10,000 or more. Cationic polymers having a weight-average molecular weight of more than 500 or more are not limited to polymers showing a single maximum value (a peak) in a molecular weight analysis by gel permeation chromatography, and polymers having a weight-average molecular weight of 500 or more may be used even if it exhibits a plural maximum value (peaks).

An amount of the cationic polymer may be in a range of from about 0.05 to 20 parts by weight against 100 parts by weight of the superabsorbent polymer particle, alternatively from about 0.3 to 10 parts by weight, and alternatively from about 0.5 to 5 parts by weight.

In some embodiments, the superabsorbent polymer particles may be coated with chitosan materials such as the one disclosed in U.S. Pat. No. 7,537,832 B2.

In some other embodiments, the superabsorbent polymer particles may comprise mixed-bed Ion-Exchange absorbent polymers such as the one disclosed in WO 99/34841 and WO 99/34842.

As already mentioned above, superabsorbent polymer particles having high SFC and FSR values do not automatically conduct to fast acquisition times of liquid exudates, especially at the first gush, i.e. when the dry superabsorbent polymer particles first come into contact with liquid. Dry superabsorbent polymer particles are typically more reluctant to absorb water than wetted superabsorbent polymer particles since the diffusivity of water into dry superabsorbent polymer particles is lower than the diffusivity of water into wetted superabsorbent polymer particles.

Hitherto, absorption properties of dry superabsorbent polymer particles related to the initial uptake has not been investigated. Rather, the focus has been on Saline Flow Conductivity (SFC), which is determined at equilibrium and thus at a stage remote from initial liquid uptake. For absorbent cores containing a significant amount of airfelt in addition to superabsorbent polymer particles, temporary storage of liquid entering the absorbent core is provided by the airfelt allowing the superabsorbent polymer particles to absorb liquid from the surrounding airfelt with a certain delay. But even for airfelt free absorbent articles disclosed in the prior art, permeability of the superabsorbent polymer particles has always been measured at equilibrium, thus not taking into account the behavior of dry superabsorbent polymer particles upon initial exposure to liquid. The inventors of the present disclosure have carefully investigated superabsorbent polymer particles behavior upon initial exposure to liquid. They have found that certain, not yet publicly available superabsorbent polymer particles exhibit superior performance when applied in absorbent cores containing no or very low amounts of airfelt. The superior performance has lead to improved liquid acquisition, thus reducing the risk of leakage. It has been found that superior superabsorbent polymer particles can be described in terms of the time it takes for dry superabsorbent polymer particles to reach a certain liquid uptake when absorbing against a confining pressure. Thereby, it is now possible to purposefully and easily select these newly developed superabsorbent polymer particles, which are specifically suitable for use in absorbent cores comprising little or no airfelt, without the need for additional extensive investigation and testing.

According to the present disclosure, the superabsorbent polymer particles comprised by the absorbent core in the front portion or the crotch portion of the article or by the whole absorbent core require a time to reach an uptake of 20 g/g (T20) of less than 240 s, or less than 215 s, or less than 190 s, or less than 165 s, or less than 140 s as measured according to the K(t) Test Method set out below.

In some embodiments, the time to reach an uptake of 20 g/g (T20) is of 40 to 240 s, or 50 to 290 s, or 60 to 165 s, as measured according to the K(t) Test Method set out below.

In some embodiments, the uptake of the superabsorbent polymer particles comprised by the absorbent core in the front portion or the crotch portion of the article or by the whole absorbent core at 20 min (U20) is of at least 28 g/g or at least 30 g/g, or of 28 g/g to 60 g/g, or of 30 g/g to 50 g/g, or of 30 g/g to 40 g/g as measured according to the K(t) Test Method set out below.

Absorbent articles comprising such superabsorbent polymer particles have improved absorption properties and therefore exhibit reduced leakage in comparison with absorbent articles of the prior art, especially at the first gush. Such superabsorbent polymer particles are particularly suitable for use in absorbent articles.

In some embodiments, the superabsorbent polymer particles have an effective permeability at 20 minutes (K20) of at least $5 \cdot 10^{-8}$ cm$^2$, or at least $7 \cdot 10^{-8}$ cm$^2$, or at least $8.5 \cdot 10^{-8}$ cm$^2$, or of $5 \cdot 10^{-8}$ cm$^2$ to $1 \cdot 10^{-6}$ cm$^2$, or of $7 \cdot 10^{-8}$ cm$^2$ to $5 \cdot 10^{-7}$ cm$^2$, or of $8.5 \cdot 10^{-8}$ to $1 \cdot 10^{-7}$ as measured according to the K(t) Test Method set out below.

In some embodiments, the superabsorbent polymer particles have a ratio between the minimum effective permeability and the permeability at 20 minutes (Kmin/K20 ratio) of more than 0.75, or more than 0.8 or more than 0.9 as measured according to the K(t) Test Method set out below. In such embodiments, the transient gel blocking is minimum and the liquid exudates are able to travel fast through the void spaces present between the particles throughout all the swelling process and especially in the initial part of the swelling phase which is the most critical for the first gush.

For embodiments having more than one type of superabsorbent polymer particles, the K(t) Test Method is carried out on a mixture of the more than one type of superabsorbent polymer particles present in the front portion or the crotch portion or the whole absorbent core respectively.

In some embodiments, the superabsorbent polymer particles have a permeability at equilibrium expressed as UPM (Urine Permeability Measurement) value of more than 50, alternatively more than 60, or of 50 to 500, or of 55 to 200, or of 60 to 150 UPM units, where 1 UPM unit is $1\times10^{-7}$ (cm$^3$·s)/g.

The UPM value is measured according to the UPM Test Method set out below. This method is closely related to the SFC test method of the prior art. The UPM Test Method typically measures the flow resistance of a preswollen layer of superabsorbent polymer particles, i.e. the flow resistance is measured at equilibrium. Therefore, such superabsorbent polymer particles having a high UPM value exhibit a high permeability when a significant volume of the absorbent article is already wetted by the liquid exudates. These embodiments exhibit good absorption properties not only at the first gush but also at the subsequent gushes.

In some embodiments, the superabsorbent polymer particles may have a FSR (Free Swell Rate) of more than 0.1 g/g/s, or of from 0.1 to 2 g/g/s, or 0.3 to 1 g/g/s, or 0.3 to 0.6 g/g/s, or 0.4 to 0.6 g/g/s.

The Free Swell Rate of the superabsorbent polymer particles is measured according to the FSR Test Method set out below. Superabsorbent polymer particles having high free swell rate values will be able to absorb liquid quickly under no confining pressure. Contrary to the K(t) Test Method, no external pressure is applied to the gel bed in order to measure the free swell rate. Superabsorbent polymer particles having a too low FSR value may not require less than 240 s to reach an uptake of 20 g/g as measured according to the K(t) Test Method of the present disclosure and will consequently not be able to absorb the liquid exudates as fast as necessary. However, as stated above, superabsorbent polymer particles having a high FSR value do not automatically lead to high uptake values as measured according to the K(t) Test Method.

In some embodiments, the superabsorbent polymer particles may have a CRC (centrifuge retention capacity) value of more than 20 g/g, or more than 24 g/g, or of from 20 to 50 g/g, or 20 to 40 g/g, or 24 to 30 g/g, as measured according to EDANA method WSP 241.2-05. The CRC measures the liquid absorbed by the superabsorbent polymer particles for free swelling in excess liquid.

Superabsorbent polymer particles having a high CRC value may be desired since less superabsorbent polymer particles are needed to facilitate a required overall capacity for liquid absorption.

In some embodiments, the absorbent article may have an acquisition time for the first gush of less than 30 s, alternatively less than 27 s, as measured according to the Flat Acquisition Test Method set out below. This acquisition time is measured on a baby diaper which is designated for wearers having a weight in the range of 8 to 13 kg±20% (such as Pampers Active Fit size 4 or other Pampers baby diapers size 4, Huggies baby diapers size 4 or baby diapers size 4 of most other tradenames). An absorbent article comprising superabsorbent polymer particles which require less than 240 s to reach an uptake of 20 g/g as measured according to the K(t) Test Method can provide faster acquisition times, especially at the first gush and thus reduced leakage, in comparison with the absorbent articles of the prior art, as shown in the Examples section of the application.

Structure of the Absorbent Core

In the following, an example for an absorbent core of the present disclosure is given. The present disclosure is however not limited to such absorbent cores.

Figure 3:
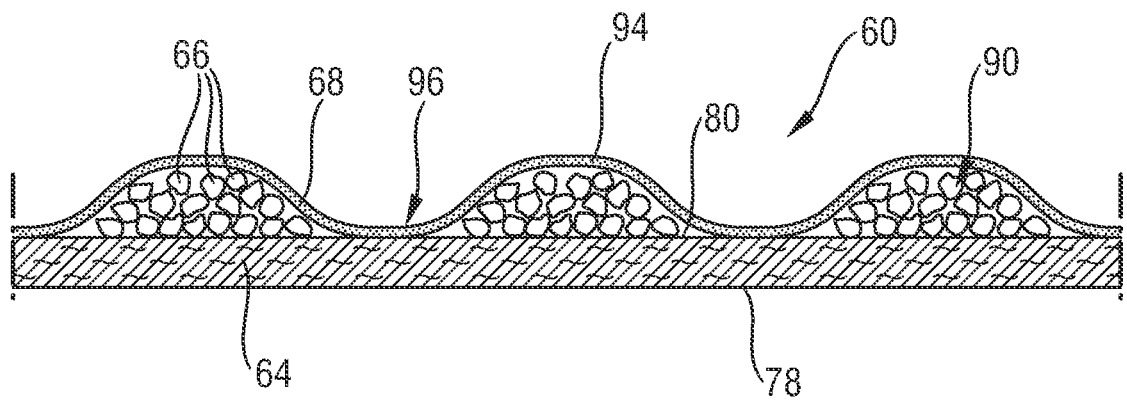
FIG. 3 is a partial cross sectional view of an absorbent core layer in accordance with an embodiment of the present disclosure.
Figure 4:
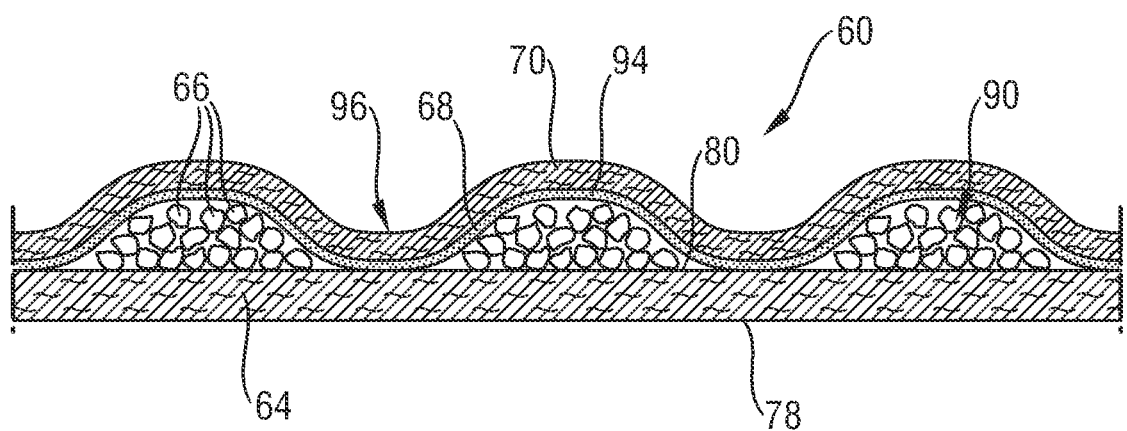
FIG. 4 is a partial cross sectional view of an absorbent core layer in accordance with another embodiment of the present disclosure.

In some embodiments, the absorbent core 14 comprises an absorbent layer 60, as illustrated in FIGS. 3 and 4. The substrate layer 64 of the absorbent layer 60 may be referred to as a dusting layer and has a first surface 78 which faces the backsheet 20 of the diaper 10 and a second surface 80 which faces the superabsorbent polymer particles 66. According to some embodiments, the substrate layer 64 is a non-woven material such as a multi-layered nonwoven material having spunbonded layers as outer layers and one or more meltblown layers in between the spunbond layers, including but not limited to SMS material, comprising a spunbonded, a meltblown and a further spunbonded layer. The absorbent layer 60 may include a cover layer 70 as illustrated in FIG. 4. The cover layer 70 may be a non-woven material such as a multi-layered nonwoven material having spunbonded layers as outer layers and one or more meltblown layers in between the spunbond layers, including but not limited to SMS material, comprising a spunbonded, a melt-blown and a further spun-bonded layer. In some embodiments, the substrate layer 64 and the cover layer 70 are made of the same material.

As illustrated in FIGS. 3 and 4, the superabsorbent polymer particles 66 can be deposited on the substrate layer 64 in clusters 90 of particles comprising land areas 94 and junction areas 96 between the land areas 94. As defined herein, land areas 94 are areas where the thermoplastic adhesive material does not contact the nonwoven substrate or the auxiliary adhesive directly; junction areas 96 are areas where the thermoplastic adhesive material does contact the nonwoven substrate or the auxiliary adhesive directly. The junction areas 96 contain little or no superabsorbent polymer particles 66. The land areas 94 and junction areas 96 can have a variety of shapes including, but not limited to, circular, oval, square, rectangular, triangular, and the like.

Thereby, the thermoplastic adhesive material 68 provides cavities to hold the superabsorbent polymer particles 66, and thereby immobilizes this material. In a further aspect, the thermoplastic adhesive material 68 bonds to the substrate layer 64 and thus affixes the superabsorbent polymer particles 66 to the substrate layer 64. In some other embodiments, the thermoplastic adhesive material 68 will also penetrate at least partly into both the superabsorbent polymer particles 66 and the substrate layer 64, thus providing for further immobilization and affixation.

Figure 5A:
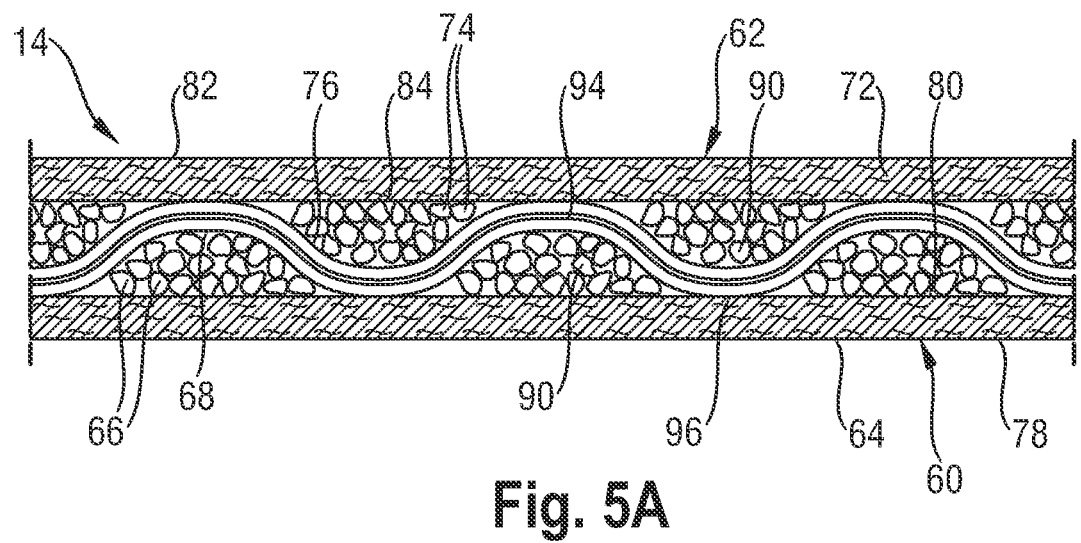
FIG. 5a is a partial sectional view of an absorbent core comprising a combination of the first and second absorbent core layers illustrated in FIGS. 3 and 4 in accordance with an embodiment of the present disclosure.
Figure 5B:
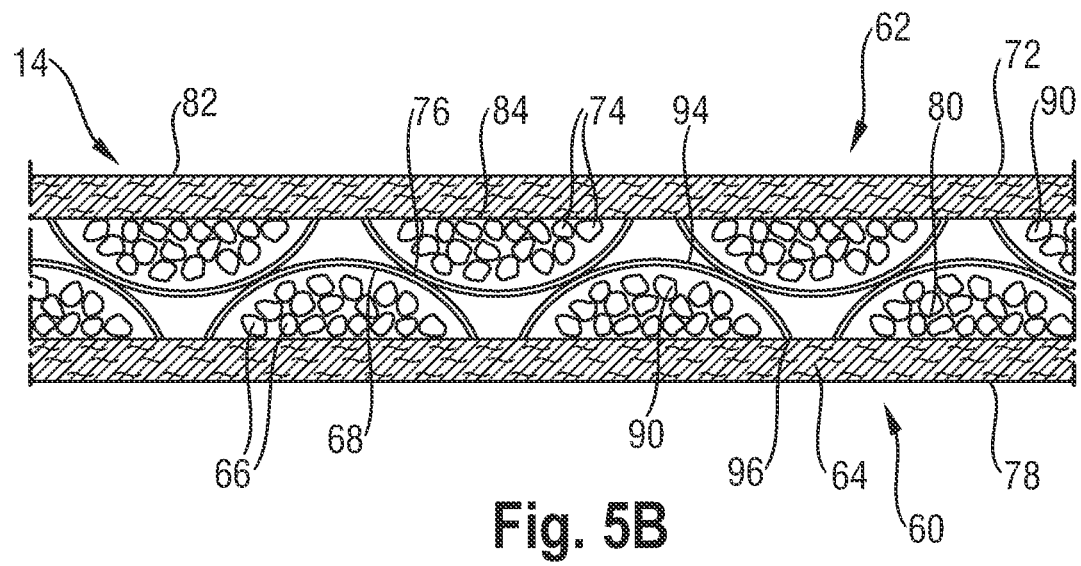
FIG. 5b is a partial sectional view of an absorbent core comprising a combination of the first and second absorbent core layers illustrated in FIGS. 3 and 4 in accordance with an embodiment of the present disclosure.

In some other embodiments, the absorbent core 14 may comprise two absorbent layers, a first absorbent layer 60 and a second absorbent layer 62. As best illustrated in FIGS. 5A and 5B, the first absorbent layer 60 of the absorbent core 14 comprises a substrate layer 64, superabsorbent polymer particles 66 on the substrate layer 64, and a thermoplastic adhesive material 68 on the superabsorbent polymer particles 66. Although not illustrated, the first absorbent layer 60 may also include a cover layer such as the cover layer 70 illustrated in FIG. 4.

Likewise, as best illustrated in FIGS. 5A and 5B, the second absorbent layer 62 of the absorbent core 14 may also include a substrate layer 72, superabsorbent polymer particles 74 on the second substrate layer 72, and a thermoplastic adhesive material 76 on the superabsorbent polymer particles 74. Although not illustrated, the second absorbent layer 62 may also include a cover layer such as the cover layer 70 illustrated in FIG. 4. As mentioned above, the substrate layer 64 of the first absorbent layer 60 may be referred to as a dusting layer and has a first surface 78 which faces the backsheet 20 of the diaper 10 and a second surface 80 which faces the superabsorbent polymer particles 66. Likewise, the substrate layer 72 of the second absorbent layer 62 may be referred to as a core cover and has a first surface 82 facing the topsheet 18 of the diaper 10 and a second surface 84 facing the superabsorbent polymer particles 74. The first and second substrate layers 64 and 72 may be adhered to one another with adhesive about the periphery to form an envelope about the superabsorbent polymer particles 66 and 74 to hold the superabsorbent polymer particles 66 and 74 within the absorbent core 14.

The area of the absorbent core 14 which comprises superabsorbent polymer particles may vary depending on the desired application of the absorbent core 14 and the particular absorbent article 10 in which it may be incorporated. In some embodiments, however, the superabsorbent polymer particles area extends substantially entirely across the absorbent core 14. In some alternative embodiments, the superabsorbent polymer particles area extends entirely across the absorbent core 14 in the crotch portion 34 of the absorbent article 10 while the superabsorbent polymer particles area does not extend entirely across the absorbent core 14 in the front and in the back portions of the absorbent article 10.

The first and second absorbent layers 60 and 62 may be combined together to form the absorbent core 14 such that the layers may be offset such that the superabsorbent polymer particles 66 on the substrate layer 64 and the superabsorbent polymer particles 74 on the substrate layer 72 are substantially continuously distributed across the superabsorbent polymer particles area, as illustrated in FIGS. 5A and 5B. In some embodiments, superabsorbent polymer particles 66 and 74 are substantially continuously distributed across the superabsorbent polymer particles area despite superabsorbent polymer particles 66 and 74 discontinuously distributed across the first and second substrate layers 64 and 72 in clusters 90. In some embodiments, the absorbent layers may be offset such that the land areas 94 of the first absorbent layer 60 face the junction areas 96 of the second absorbent layer 62 and the land areas of the second absorbent layer 62 face the junction areas 96 of the first absorbent layer 60, as illustrated in FIGS. 5A and 5B. When the land areas 94 and junction areas 96 are appropriately sized and arranged, the resulting combination of superabsorbent polymer particles 66 and 74 is a substantially continuous layer of superabsorbent polymer particles across the superabsorbent polymer particles area of the absorbent core 14 (i.e. first and second substrate layers 64 and 72 do not form a plurality of pockets, each containing a cluster 90 of superabsorbent polymer particles 66 and 74 therebetween), as shown on FIG. 5A.

The amount of superabsorbent polymer particles may or not vary along the length of the core, typically the core being profiled in its longitudinal direction. It has been found that, for most absorbent articles such as diapers, the liquid discharge occurs predominately in the front half of the diaper. The front half of the absorbent core 14 should therefore comprise most of the absorbent capacity of the core. Thus, according to certain embodiments, the front half of said absorbent core 14 may comprise more than about 60% of the superabsorbent polymer particles, or more than about 65%, 70%, 75%, 80%, 85%, or 90% of the superabsorbent polymer particles.

Typically the thermoplastic adhesive material may serve to at least partially immobilize the superabsorbent polymer particles both in dry and wet state. The thermoplastic adhesive material can be disposed essentially uniformly between the superabsorbent polymer particles. However, typically the thermoplastic adhesive material may be provided as a fibrous layer which is at least partially in contact with the superabsorbent polymer particles and partially in contact with the substrate layer(s). Typically, the thermoplastic adhesive material of the present disclosure forms a fibrous network over the superabsorbent polymer particles. Typically as for example illustrated in FIGS. 5A and 5B, the superabsorbent polymer particles 66 and 74 are provided as a discontinuous layer, and a layer of fibrous thermoplastic adhesive material 68 and 76 is laid down onto the layer of superabsorbent polymer particles 66 and 74, such that the thermoplastic adhesive material 68 and 76 is in direct contact with the superabsorbent polymer particles 66 and 74, but also in direct contact with the second surfaces 80 and 84 of the substrate layers 64 and 72, where the substrate layers are not covered by the superabsorbent polymer particles 66 and 74. This imparts an essentially three-dimensional structure to the fibrous layer of thermoplastic adhesive material 68 and 76, which in itself is essentially a two-dimensional structure of relatively small thickness, as compared to the dimension in length and width directions. In other words, the thermoplastic adhesive material 68 and 76 undulates between the superabsorbent polymer particles 68 and 76 and the second surfaces of the substrate layers 64 and 72.

The thermoplastic adhesive material may provide cavities to enlace the superabsorbent polymer particles, and thereby immobilizes these particles. In a further aspect, the thermoplastic adhesive material bonds to the substrate layer(s) and thus affixes the superabsorbent polymer particles to the substrate layer(s). Some thermoplastic adhesive materials will also penetrate into both the superabsorbent polymer particles and the substrate layer(s), thus providing for further immobilization and affixation. Of course, while the thermoplastic adhesive materials disclosed herein provide an improved wet immobilization (i.e., immobilization of absorbent material when the article is at least partially loaded), these thermoplastic adhesive materials may also provide a very good immobilization of absorbent material when the absorbent core is dry. The thermoplastic adhesive material may also be referred to as a hot melt adhesive.

Without wishing to be bound by theory, it has been found that those thermoplastic adhesive materials which are most useful for immobilizing the superabsorbent polymer particles combine good cohesion and good adhesion behavior. Good adhesion may promote good contact between the thermoplastic adhesive material and the superabsorbent polymer particles and the substrate layer(s). Good cohesion reduces the likelihood that the adhesive breaks, in particular in response to external forces, and namely in response to strain. When the absorbent core absorbs liquid, the superabsorbent polymer particles swell and subject the thermoplastic adhesive material to external forces. The thermoplastic adhesive material may allow for such swelling, without breaking and without imparting too many compressive forces, which would restrain the superabsorbent polymer particles from swelling.

The thermoplastic adhesive material may comprise, in its entirety, a single thermoplastic polymer or a blend of thermoplastic polymers, having a softening point, as determined by the ASTM Method D-36-95 "Ring and Ball", in the range between 50° C. and 300° C., or alternatively the thermoplastic adhesive material may be a hot melt adhesive comprising at least one thermoplastic polymer in combination with other thermoplastic diluents such as tackifying resins, plasticizers and additives such as antioxidants. In some embodiments, the thermoplastic polymer has typically a molecular weight (Mw) of more than 10,000 and a glass transition temperature (Tg) usually below room temperature or −6° C.>Tg<16° C. In some embodiments, typical concentrations of the polymer in a hot melt are in the range of about 20 to about 40% by weight. In some embodiments, thermoplastic polymers may be water insensitive. Exemplary polymers are (styrenic) block copolymers including A-B-A triblock structures, A-B diblock structures and (A-B)n radial block copolymer structures wherein the A blocks are non-elastomeric polymer blocks, typically comprising polystyrene, and the B blocks are unsaturated conjugated diene or (partly) hydrogenated versions of such. The B block is typically isoprene, butadiene, ethylene/butylene (hydrogenated butadiene), ethylene/propylene (hydrogenated isoprene), or a mixture thereof.

Other suitable thermoplastic polymers that may be employed are metallocene polyolefins, which are ethylene polymers prepared using single-site or metallocene catalysts. Therein, at least one comonomer can be polymerized with ethylene to make a copolymer, terpolymer or higher order polymer. Also applicable are amorphous polyolefins or amorphous polyalphaolefins (APAO) which are homopolymers, copolymers or terpolymers of C2 to C8 alpha olefins.

In some embodiments, the thermoplastic adhesive material is present in the form of fibers. In some of these embodiments, the fibers will have an average thickness of about 1 to about 50 micrometers or about 1 to about 35 micrometers and an average length of about 5 mm to about 50 mm or about 5 mm to about 30 mm. To improve the adhesion of the thermoplastic adhesive material to the substrate layer(s) or to any other layer, in particular any other non-woven layer, such layers may be pre-treated with an auxiliary adhesive.

In certain embodiments the thermoplastic adhesive material is applied on the substrate layer at an amount of between 0.5 and 30 g/m2, between 1 to 15 g/m2, between 1 and 10 g/m2 or even between 1.5 and 5 g/m2 per substrate layer.

An exemplary thermoplastic adhesive material 68 and 76 may have a storage modulus G' measured at 20° C. of at least 30,000 Pa and less than 300,000 Pa, or less than 200,000 Pa, or between 140,000 Pa and 200,000 Pa, or less than 100,000 Pa. In a further aspect, the storage modulus G' measured at 35° C. may be greater than 80,000 Pa. In a further aspect, the storage modulus G' measured at 60° C. may be less than 300,000 Pa and more than 18,000 Pa, or more than 24,000 Pa, or more than 30,000 Pa, or more than 90,000 Pa. In a further aspect, the storage modulus G' measured at 90° C. may be less than 200,000 Pa and more than 10,000 Pa, or more than 20,000 Pa, or more then 30,000 Pa. The storage modulus measured at 60° C. and 90° C. may be a measure for the form stability of the thermoplastic adhesive material at elevated ambient temperatures. This value is particularly important if the absorbent product is used in a hot climate where the thermoplastic adhesive material would lose its integrity if the storage modulus G' at 60° C. and 90° C. is not sufficiently high.

Figure 6:
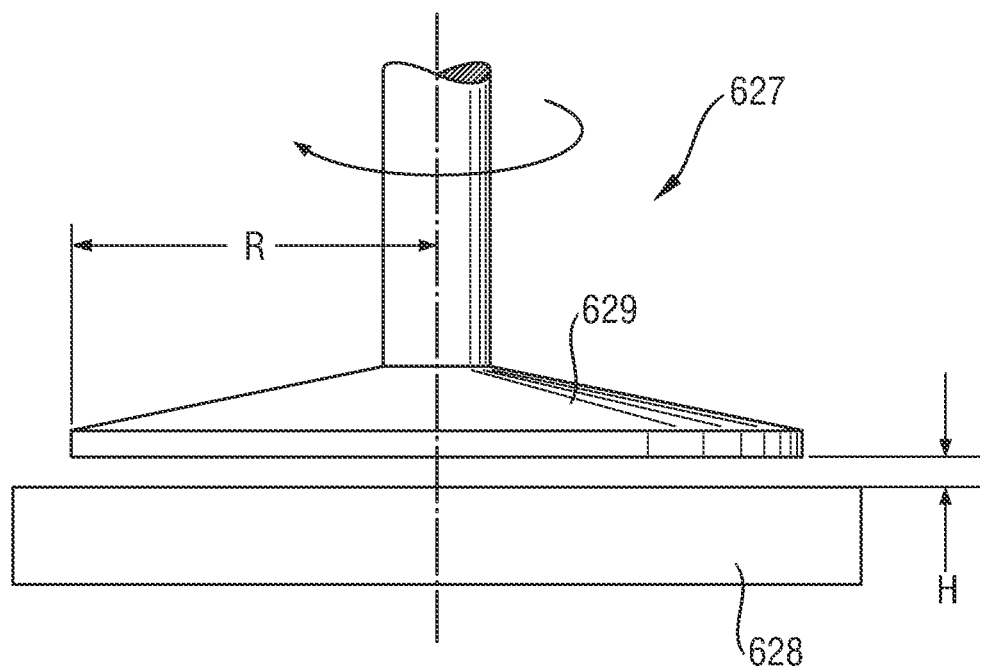
FIG. 6 is a schematic representation of a rheometer.

G' is measured using a rheometer as schematically illustrated in FIG. 6 for the purpose of general illustration only. The rheometer 627 is capable of applying a shear stress to the adhesive and measuring the resulting strain (shear deformation) response at constant temperature. The adhesive is placed between a Peltier-element acting as lower, fixed plate 628 and an upper plate 629 with a radius R of 10 mm, which is connected to the drive shaft of a motor to generate the shear stress. The gap between both plates has a height H of 1500 micron. The Peltier-element enables temperature control of the material (+0.5° C.). The strain amplitude is set at 0.05%, the strain frequency at 1 Hz and the cooling rate at 2° C./min (with start temperature at 150° C. or higher and end temperature at −5° C.).

The absorbent core may also comprise an auxiliary adhesive which is not illustrated in the figures. The auxiliary adhesive may be deposited on the substrate layer(s) before application of the superabsorbent polymer particles on the substrate layer(s) for enhancing adhesion of the superabsorbent polymer particles and the thermoplastic adhesive material to the respective substrate layer. The auxiliary adhesive may also aid in immobilizing the superabsorbent polymer particles and may comprise the same thermoplastic adhesive material as described hereinabove or may also comprise other adhesives including but not limited to sprayable hot melt adhesives. An example of commercially available auxiliary adhesive is H.B. Fuller Co. (St. Paul, Minn.) Product No. HL-1620-B. The auxiliary adhesive may be applied to the substrate layer(s) by any suitable means, but according to some embodiments, may be applied in about 0.5 to about 1 mm wide slots spaced about 0.5 to about 2 mm apart.

The Acquisition System

Figure 2:
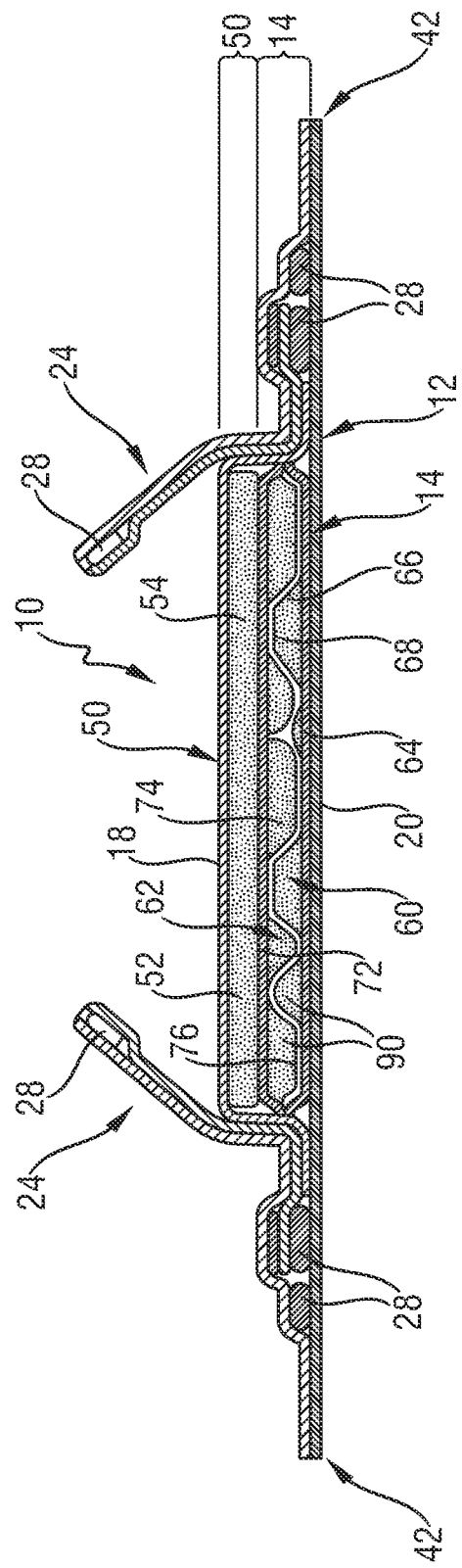
FIG. 2 is a cross sectional view of the diaper shown in FIG. 1 taken along the sectional line 2-2 of FIG. 1 in accordance with an embodiment of the present disclosure.

In some embodiments, the absorbent article 10 may comprise an acquisition system 50 which is disposed between the topsheet 18 and the absorbent core 14, as illustrated in FIGS. 1 and 2. The acquisition system 50 may not comprise any superabsorbent polymer particles.

The acquisition system 50 may be in direct contact with the absorbent core 14. The acquisition system 50 may comprise a single layer or multiple layers, such as an upper acquisition layer 52 facing towards the wearer's skin and a lower acquisition layer 54 facing the garment of the wearer, as illustrated in FIGS. 1 and 2. In some embodiments, the acquisition system 50 may function to receive a surge of liquid, such as a gush of urine. In other words, the acquisition system 50 may serve as a temporary reservoir for liquid until the absorbent core 14 can absorb the liquid.

In some embodiments, the acquisition system 50 may comprise chemically cross-linked cellulosic fibers. Such cross-linked cellulosic fibers may have desirable absorbency properties. Exemplary chemically cross-linked cellulosic fibers are disclosed in U.S. Pat. No. 5,137,537. In some embodiments, the chemically cross-linked cellulosic fibers are cross-linked with between about 0.5 mole % and about 10.0 mole % of a $C_2$ to $C_9$ polycarboxylic cross-linking agent or between about 1.5 mole % and about 6.0 mole % of a $C_2$ to $C_9$ polycarboxylic cross-linking agent based on glucose unit. Citric acid is an exemplary cross-linking agent. In some other embodiments, polyacrylic acids may be used. In some embodiments, the cross-linked cellulosic fibers may further have a water retention value of about 25 to about 60, or about 28 to about 50, or about 30 to about 45. A method for determining water retention value is disclosed in U.S. Pat. No. 5,137,537. In some embodiments, the cross-linked cellulosic fibers may be crimped, twisted, or curled, or a combination thereof including crimped, twisted, and curled.

In some embodiments, one or both of the upper and lower acquisition layers 52 and 54 may comprise a non-woven, which may be hydrophilic. Further, according to a certain embodiment, one or both of the upper and lower acquisition layers 52 and 54 may comprise the chemically cross-linked cellulosic fibers, which may or may not form part of a non-woven material.

In some embodiments, the upper acquisition layer 52 may consist of a nonwoven, without the cross-linked cellulosic fibers, and the lower acquisition layer 54 may comprise the chemically cross-linked cellulosic fibers. In some embodiments, the lower acquisition layer 54 may comprise the chemically cross-linked cellulosic fibers mixed with other fibers such as natural or synthetic polymeric fibers. In some embodiments, such other natural or synthetic polymeric fibers may include high surface area fibers, thermoplastic binding fibers, polyethylene fibers, polypropylene fibers, PET fibers, rayon fibers, lyocell fibers, and mixtures thereof.

In some embodiment, the lower acquisition layer 54 desirably has a high fluid uptake capability. Fluid uptake is measured in grams of absorbed fluid per gram of absorbent material and is expressed by the value of "maximum uptake." A high fluid uptake corresponds therefore to a high capacity of the material and is beneficial, because it ensures the complete acquisition of fluids to be absorbed by an acquisition material. In some embodiments, the lower acquisition layer 54 has a maximum uptake of about 10 g/g.

An attribute of the upper acquisition layer 52 is its Median Desorption Pressure, MDP. The MDP is a measure of the capillary pressure that is required to dewater the lower acquisition layer 54 to about 50% of its capacity at 0 cm capillary suction height under an applied mechanical pressure of 0.3 psi. Generally, a relatively lower MDP may be useful. The lower MDP may allow the lower acquisition layer 54 to more efficiently drain the upper acquisition material. Without wishing to be bound by theory, a given distribution material may have a definable capillary suction. The ability of the lower acquisition layer 54 to move liquid vertically via capillary forces will be directly impacted by gravity and the opposing capillary forces associated with desorption of the upper acquisition layer 52. Minimizing these capillary forces may positively impact the performance of the lower acquisition layer 54. However, in some embodiments, the lower acquisition layer 54 may also have adequate capillary absorption suction in order to drain the layers above (upper acquisition layer 52 and topsheet 18, in particular) and to temporarily hold liquid until the liquid can be partitioned away by the absorbent core components. Therefore, in some embodiments, the lower acquisition layer 54 may have a minimum MDP of greater than 5 cm $H_2O$. Further, according to exemplary embodiments, the lower acquisition layer 54 has an MDP value of less than about 20.5 cm $H_2O$, alternatively less than about 19 cm $H_2O$, and alternatively less than about 18 cm $H_2O$ to provide for fast acquisition.

The methods for determining MDP and maximum uptake are disclosed in U.S. Patent Application No. 2007/0118087 (Flohr et al.). For example, according to a first embodiment, the lower acquisition layer 54 may comprise about 70% by weight of chemically cross-linked cellulose fibers, about 10% by weight polyester (PET), and about 20% by weight untreated pulp fibers. According to a second embodiment, the lower acquisition layer 54 may comprise about 70% by weight chemically cross-linked cellulose fibers, about 20% by weight lyocell fibers, and about 10% by weight PET fibers. According to a third embodiment, the lower acquisition layer 54 may comprise about 68% by weight chemically cross-linked cellulose fibers, about 16% by weight untreated pulp fibers, and about 16% by weight PET fibers. In one embodiment, the lower acquisition layer 54 may comprise from about 90-100% by weight chemically cross-linked cellulose fibers.

Suitable non-woven materials for the upper and lower acquisition layers 52 and 54 include, but are not limited to SMS material, comprising a spunbonded, a melt-blown and a further spunbonded layer. In certain embodiments, permanently hydrophilic non-wovens, and in particular, nonwovens with durably hydrophilic coatings are desirable. Another suitable embodiment comprises a SMMS-structure. In some embodiments, the nonwovens are carded resin-bonded. In certain embodiments, the non-wovens are porous.

In some embodiments, suitable non-woven materials may include, but are not limited to synthetic fibers, such as PE, PET, and PP. As polymers used for nonwoven production may be inherently hydrophobic, they may be coated with hydrophilic coatings. One way to produce nonwovens, with durably hydrophilic coatings, is via applying a hydrophilic monomer and a radical polymerization initiator onto the nonwoven, and conducting a polymerization activated via UV light resulting in monomer chemically bound to the surface of the nonwoven as described in U.S. Patent Publication No. 2005/0159720. Another way to produce nonwovens with durably hydrophilic coatings is to coat the nonwoven with hydrophilic nanoparticles as described in U.S. Pat. No. 7,112,621 to Rohrbaugh et al. and in PCT Application Publication WO 02/064877.

Further useful non-wovens are described in U.S. Pat. No. 6,645,569 to Cramer et al., U.S. Pat. No. 6,863,933 to Cramer et al., U.S. Pat. No. 7,112,621 to Rohrbaugh et al., and U.S. Patent Application No. 2003/0148684 to Cramer et al. and U.S. Patent Application No. 2005/0008839 to Cramer et al.

In some cases, the nonwoven surface can be pre-treated with high energy treatment (corona, plasma) prior to application of nanoparticle coatings. High energy pre-treatment typically temporarily increases the surface energy of a low surface energy surface (such as PP) and thus enables better wetting of a nonwoven by the nanoparticle dispersion in water.

Notably, permanently hydrophilic non-wovens are also useful in other parts of an absorbent article. For example, topsheets and absorbent core layers comprising permanently hydrophilic non-wovens as described above have been found to work well.

In some embodiment, the upper acquisition layer 52 may comprise a material that provides good recovery when external pressure is applied and removed. In some embodiments, the upper acquisition layer 52 may comprise a blend of different fibers selected, for example from the types of polymeric fibers described above. In some embodiments, at least a portion of the fibers may exhibit a spiral-crimp which has a helical shape. In some embodiments, the upper acquisition layer 52 may comprise fibers having different degrees or types of crimping, or both. For example, some embodiments may include a mixture of fibers having about 8 to about 12 crimps per inch (cpi) or alternatively about 9 to about 10 cpi, and other fibers having about 4 to about 8 cpi or alternatively about 5 to about 7 cpi. Different types of crimps include, but are not limited to a 2D crimp or "flat crimp" and a 3D or spiral-crimp. In some embodiments, the fibers may include bi-component fibers, which are individual fibers each comprising different materials, usually a first and a second polymeric material. It is believed that the use of side-by-side bi-component fibers is beneficial for imparting a spiral-crimp to the fibers.

The upper acquisition layer 52 may be stabilized by a latex binder, for example a styrene-butadiene latex binder (SB latex), in a certain embodiment. Processes for obtaining such lattices are known, for example, from EP 149 880 (Kwok) and US 2003/0105190 (Diehl et al.). In certain embodiments, the binder may be present in the upper acquisition layer 52 in excess of about 12%, about 14% or about 16% by weight. For certain embodiments, SB latex is available under the trade name GENFLO™ 3160 (OMNOVA Solutions Inc.; Akron, Ohio).

The Topsheet

The absorbent article 10 may comprise a topsheet 18 which may be liquid pervious. The topsheet 18 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be included of natural fibers (e.g., wood or cotton fibers), synthetic fibers (e.g., polymeric fibers such as polyester, polypropylene, or polyethylene fibers) or from a combination of natural and synthetic fibers.

In some embodiments, the topsheet 18 may be made of a hydrophobic material to isolate the wearer's skin from liquids which have passed through the topsheet 18. In such embodiments, at least a part of the upper surface of the topsheet 18 is treated to be hydrophilic so that liquids will transfer through the topsheet 18 more rapidly. This diminishes the likelihood that body exudates will flow off the topsheet 18 rather than being drawn through the topsheet 18 and being absorbed by the absorbent core. The topsheet 18 can be rendered hydrophilic by treating it with a surfactant. Suitable methods for treating the topsheet 18 with a surfactant include spraying the topsheet material with the surfactant and immersing the material into the surfactant.

In some embodiments, the topsheet includes an apertured formed film. Apertured formed films are pervious to body exudates and yet non-absorbent and have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films are described in U.S. Pat. No. 3,929,135, entitled "Absorptive Structures Having Tapered Capillaries", issued to Thompson on Dec. 30, 1975; U.S. Pat. No. 4,324,246 entitled "Disposable Absorbent Article Having A Stain Resistant Topsheet", issued to Mullane, et al. on Apr. 13, 1982; U.S. Pat. No. 4,342,314 entitled "Resilient Plastic Web Exhibiting Fiber-Like Properties", issued to Radel, et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression", issued to Ahr, et al. on Jul. 31, 1984; and U.S. Pat. No. 5,006,394 "Multilayer Polymeric Film" issued to Baird on Apr. 9, 1991.

Alternatively, the topsheet includes apertured nonwoven materials. Suitable apertured nonwoven materials are described in U.S. Pat. No. 5,342,338 and in PCT Application No. WO 93/19715.

The Backsheet

The absorbent article may comprise a backsheet 20 which may be attached to the topsheet.

The backsheet may prevent the exudates absorbed by the absorbent core and contained within the diaper from soiling other external articles that may contact the diaper, such as bed sheets and undergarments. In some embodiments, the backsheet may be substantially impervious to liquids (e.g., urine) and comprise a laminate of a nonwoven and a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names X15306, X10962, and X10964. Other suitable backsheet materials may include breathable materials that permit vapors to escape from the diaper while still preventing liquid exudates from passing through the backsheet. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746, published on Jun. 22, 1995 in the name of E. I. DuPont. Other breathable backsheets including nonwoven webs and apertured formed films are described in U.S. Pat. No. 5,571,096 issued to Dobrin et al. on Nov. 5, 1996.

Test Methods

K(t) Test Method (Dynamic Effective Permeability and Uptake Kinetics Measurement Test Method)

This method determines the time dependent effective permeability (K(t)) and the uptake kinetics of a gel layer formed from hydrogel-forming superabsorbent polymer particles or of an absorbent structure containing such particles under a confining pressure. The objective of this method is to assess the ability of the gel layer formed from hydrogel-forming superabsorbent polymer particles or the absorbent structure containing them to acquire and distribute body fluids when the polymer is present at high concentrations in an absorbent article and exposed to mechanical pressures as they typically occur during use of the absorbent article. Darcy's law and steady-state flow methods are used to calculate effective permeability (see below). (See also for example, "Absorbency," ed. by P. K. Chatterjee, Elsevier, 1982, Pages 42-43 and "Chemical Engineering Vol. II, Third Edition, J. M. Coulson and J. F. Richardson, Pergamon Press, 1978, Pages 122-127.)

In contrast to previously published methods, the sample is not preswollen therefore the hydrogel is not formed by pre-swelling hydrogel-forming superabsorbent polymer particles in synthetic urine, but the measurement is started with a dry structure.

The equipment used for this method is called 'Zeitabhängiger Durchlässigkeitsprüfstand' or 'Time Dependent Permeability Tester', Equipment No. 03-080578 and is commercially available at BRAUN GmbH, Frankfurter Str. 145, 61476 Kronberg, Germany and is described below. Upon request, operating instructions, wiring diagrams and detailed technical drawings are also available.

Dynamic Effective Permeability and Uptake Kinetic Measurement System

Figure 7:
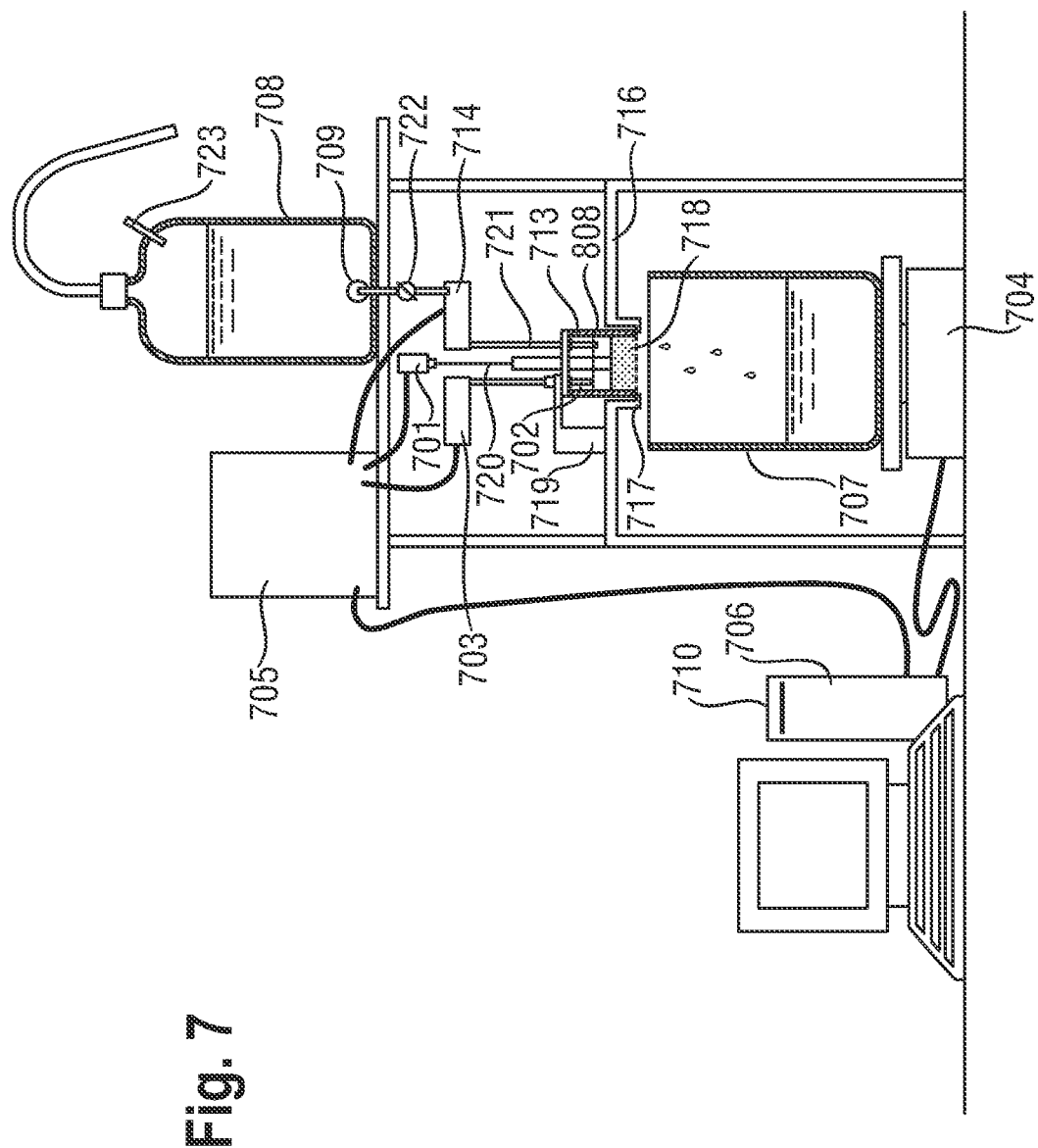
FIG. 7 is a partial cross-sectional side view of a suitable permeability measurement system for conducting the Dynamic Effective Permeability and Uptake Kinetics Measurement Test.

FIG. 7 shows the dynamic effective permeability and uptake kinetic measurement system, called 'Time Dependent Permeability Tester' herein.

The equipment consists of the following main parts:

M11 Digital Laser Sensor for caliper measurement 701 (MEL Mikroelektronik GmbH, 85386 Eching, Germany Fiber for Liquid Level Detection 702 (FU95, Keyence Corp., Japan)

Digital Fiber Sensor 703 (FS-N10, Keyence Corp., Japan)

Precision Balance 704 (XP6002MDR, Mettler Toledo AG, 8606 Greifensee, Switzerland)

Power Unit Logo!Power (C98130-A7560-A1-5-7519, Siemens AG)

Labview Software License 706 (National Instruments, Austin, Tx, USA)

Receiving Vessel 707 (5 L Glass Beaker, Roth)

Reservoir 708 (5 L Glass bottle, VWR) with joint 709 and open-end tube for air admittance 723

Operating unit and console 705 (Conrad Electronics)

Computerized data acquisition system 710

A piston/cylinder assembly 713 as described herein

A controlled valve 714 (Burkert)

Figure 8:
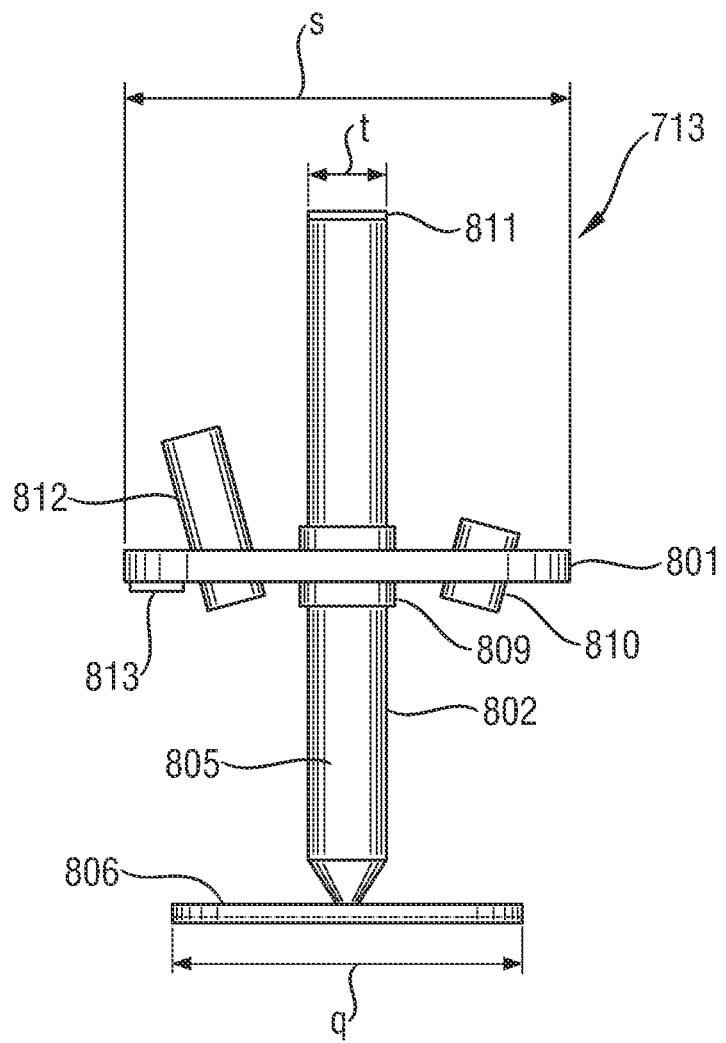
FIG. 8 is a cross-sectional side view of a piston/cylinder assembly for use in conducting the Dynamic Effective Permeability and Uptake Kinetics Measurement Test.
Figure 8:
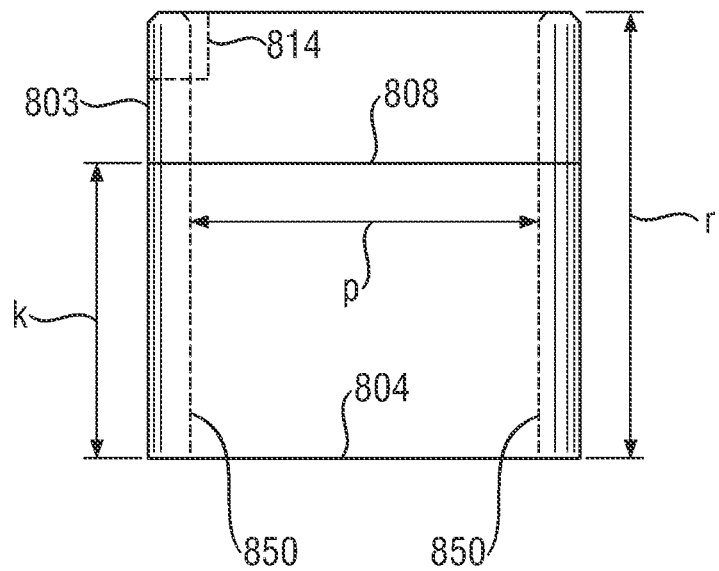
Figure 9:
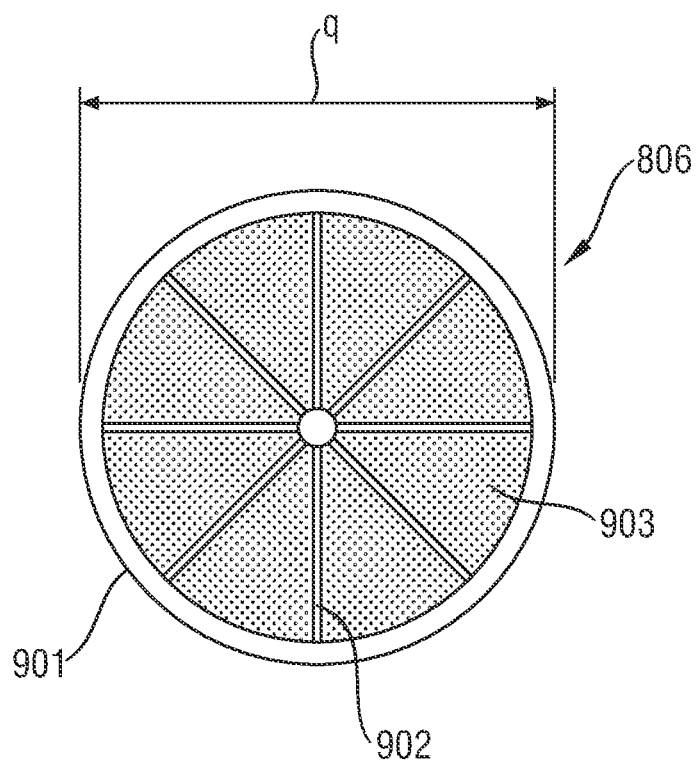
FIG. 9 is a top view of a piston head suitable for use in the piston/cylinder assembly shown in FIG. 8.

FIG. 8 shows the piston/cylinder assembly 713 comprising piston guiding lid 801, piston 802 and cylinder 803. The cylinder 803 is made of transparent polycarbonate (e.g., Lexan®) and has an inner diameter p of 6.00 cm (area=28.27 cm²). The inner cylinder walls 850 are smooth; the height of the cylinder r is about 7.50 cm. The bottom 804 of the cylinder 803 is faced with a US. Standard 400 mesh stainless-steel screen cloth (not shown) (e.g. from Weisse and Eschrich) that is bi-axially stretched to tautness prior to attachment to the bottom 804 of the cylinder 803. The piston 802 is composed of a stainless steel piston body 805 and a stainless steel head 806. The piston head 806 diameter q is slightly less than 6 cm so as to slide freely into the cylinder 803 without leaving any gap for the hydrogel-forming particle to pass trough. The piston body 805 is firmly attached perpendicularly at the center of the piston head 806. The piston body diameter t is about 2.2 cm. The piston body 805 is then inserted into a piston guiding lid 801. The guiding lid 801 has a POM (Polyoxymethylene) ring 809 with a diameter allowing a free sliding of the piston 802 yet keeping the piston body 805 perfectly vertical and parallel to the cylinder walls 850 once the piston 802 with the guiding lid 801 are positioned on top of the cylinder 803. The top view of the piston head 806 is shown in FIG. 9. The piston head 806 is meant to apply the pressure homogeneously to the sample 718. It is also highly permeable to the hydrophilic liquid so as to not limit the liquid flow during measurement. The piston head 806 is composed of a US. standard 400 mesh stainless steel screen cloth 903 (e.g. from Weisse and Eschrich) that is bi-axially stretched to tautness and secured at the piston head stainless steel outer ring 901. The entire bottom surface of the piston is flat. Structural integrity and resistance to bending of the mesh screen is then ensured by the stainless steel radial spokes 902. The height of the piston body 805 is selected such that the weight of the piston 802 composed of the piston body 805 and the piston head 806 is 596 g (±6 g), this corresponds to 0.30 psi over the area of the cylinder 803.

The piston guiding lid 801 is a flat circle of stainless steel with a diameter s of about 7.5 cm held perpendicular to the piston body 805 by the POM ring 809 in its center. There are two inlets in the guiding lid (810 and 812).

The first inlet 812, allows the Fiber for Liquid Level Detection 702 to be positioned exactly 5 cm above the top surface of the screen (not shown) attached to the bottom (804) of the cylinder 803 once the piston 802 is assembled with the cylinder 803 for the measurement.

The second inlet 810 allows connecting a liquid tube 721 providing the liquid to the experiment.

To make sure that the assembly of the piston 802 with the cylinder 803 is done consistently a slit 814 is made on the cylinder 803 matching a position marker 813 in the guiding lid 801. In this way the rotation angle of the cylinder and the guiding lid is always the same.

Prior to every use, the stainless steel screen cloth 903 of the piston head 806 and cylinder 803 should be inspected for clogging, holes or over-stretching and replaced when necessary. A K(t) apparatus with damaged screen can deliver erroneous K(t) and uptake kinetic results, and must not be used until the screen has been replaced.

A 5 cm mark 808 is scribed on the cylinder at a height k of 5.00 cm (±0.02 cm) above the top surface of the screen attached to the bottom 804 of the cylinder 803. This marks the fluid level to be maintained during the analysis. The Fiber for Liquid Level Detection 702 is positioned exactly at the 5 cm mark 808. Maintenance of correct and constant fluid level (hydrostatic pressure) is critical for measurement accuracy A reservoir 708 connected via tubing to the piston/cylinder assembly 713 holding the sample and a controller valve 714 are used to deliver salt solution to the cylinder 803 and to maintain the level of salt solution at a height k of 5.00 cm above the top surface of screen attached to the bottom of the cylinder 804. The valve 714, the Fiber for Liquid Level Detection 702 and the Digital Fiber Sensor 703 are connected to the computerized acquisition system 710 trough the operating unit 705. This allows the Dynamic Effective Permeability and Uptake Kinetic Measurement System to use the information from the Fiber for Liquid Level Detection 702 and the Digital Fiber Sensor 703 to control the valve 714 and ultimately maintain the level of the liquid at the 5 cm mark 808.

The reservoir 708 is placed above the piston/cylinder assembly 713 in such a manner as to allow a 5 cm hydrohead to be formed within 15 seconds of initiating the test, and to be maintained in the cylinder throughout the test procedure. The piston/cylinder assembly 713 is positioned on the support ring 717 of the cover plate 716 and the first inlet 812 is held in place with the docking support 719. This allows only one position of the guiding lid 801. Furthermore, due to the position marker 813, there is also only one position for the cylinder 803. The screen attached to the bottom of the cylinder 804 must be perfectly level and horizontal. The supporting ring 717 needs to have an internal diameter small enough, so to firmly support cylinder 803 but larger than 6.0 cm so to lay outside of the internal diameter of the cylinder once the cylinder is positioned on the supporting ring 717. This is important so to avoid any interference of the supporting ring 717 with the liquid flow.

The salt solution, applied to the sample 718 with a constant hydrohead of 5 cm can now freely flow from the piston/cylinder assembly 713 into a receiving vessel 707 positioned on the balance 704 which is accurate within ±0.01 g. The digital output of the balance is connected to a computerized data acquisition system.

The caliper (thickness) of the sample is constantly measured with a Digital Laser Sensor for caliper measurement 701. The laser beam 720 of the digital laser sensor 701 is directed at the center of the POM cover plate 811 of the piston body. The accurate positioning of all the parts of the piston/cylinder assembly 713 allows the piston body 805 to be perfectly parallel to the laser beam 720 and as a result an accurate measure of the thickness is obtained.

Test Preparation

The reservoir 708 is filled with test solution. The test solution is an aqueous solution containing 9.00 grams of sodium chloride and 1.00 grams of surfactant per liter of solution. The preparation of the test solution is described below. The receiving vessel 707 is placed on the balance 704 which is connected to a computerized data acquisition system 710. Before the start of the measurement the balance is reset to zero.

Preparation of Test Liquid:

Chemicals needed:

Sodium Chloride (CAS #7647-14-5, e.g.: Merck, cat #1.06404.1000)

Linear $C_{12}$-$C_{14}$ alcohol ethoxylate (CAS #68439-50-9, e.g. Lorodac®, Sasol, Italy)

Deionized $H_2O$

Ten liters of a solution containing 9.00 grams per liter of NaCl and 1.00 grams per liter linear $C_{12}$-$C_{14}$ alcohol ethoxalate in distilled water is prepared and equilibrated at 23° C.±1° C. for 1 hour. The surface tension is measured on 3 individual aliquots and should be 28±0.5 mN/m. If the surface tension of the solution is different from 28±0.5 mN/m, the solution is discarded and a new test solution is prepared. The test solution has to be used within 36 hours from its preparation and is considered expired afterwards.

K(t) Sample Preparation

A 10 grams representative sample of the superabsorbent polymer particles is obtained. This is then dried in an uncovered 10 cm diameter Petri dish in a vacuum chamber at 23±2°

C. and 0.01 Torr or lower for 48 hours prior to use. The sample is removed from the vacuum chamber and immediately stored in a tightly sealed 20 mL glass airtight container at 23±2° C. until further use.

2.0 g (±0.02 g) of superabsorbent polymer particles are weighed onto a suitable weighing paper using an analytical balance and transferred to the cylinder 803 with the particles distributed evenly on the screen (not shown) attached to the bottom 804 of the cylinder 803. This is done via sprinkling the superabsorbent polymer, while at the same time turning the cylinder clockwise (e.g. on a circular turning table schuett petriturn-M available at Schuett-biotec GmbH, Rudolf-Wissell-Str. 13 D-37079 Gottingen Germany). An even distribution of the superabsorbent polymer particles is critical for the measurements accuracy.

K(t) Procedure

The measurement is carried out at Tappi lab conditions: 23° C.±1° C./50% RH±2%.

The empty piston/cylinder assembly 713 is mounted in the circular opening in the cover plate 716 and is supported around its lower perimeter by the supporting ring 717. The piston/cylinder assembly 713 is held in place with the docking support 719 with the cylinder 803 and piston 802 aligned at the proper angle. The reference caliper reading ($r_r$) is measured by Digital Laser sensor. After this, the empty piston/cylinder assembly 713 is removed from the cover plate 716 and supporting ring 717 and the piston 802 is removed from the cylinder 803.

The sample 718 is positioned (absorbent structure) or sprinkled (superabsorbent polymer particles) on the cylinder screen as explained above. After this, the piston 802 assembled with the guiding lid 801 is carefully set into the cylinder 803 by matching the position marker 813 of the guiding lid 801 with the slit 814 made in the cylinder 803.

The piston/cylinder assembly is held in place with the docking support 719 with the cylinder and piston aligned at the proper angle.

This can be only done in one way. The liquid tube 721 connected to the reservoir 708 and the Digital Fiber Sensor 703 are inserted into the piston/cylinder assembly 713 via the two inlets 810 and 812 in the guiding lid 801.

The computerized data acquisition system 710 is connected to the balance 704 and to the digital laser sensor for caliper measurement 701. Fluid flow from the reservoir 708 to the cylinder 803 is initiated by the computer program by opening valve 714. The cylinder is filled until the 5 cm mark 808 is reached in 5 to 15 seconds, after which the computer program regulates the flow rate to maintain a constant 5 cm hydrohead. The quantity of solution passing through the sample 718 is measured by the balance 704 and the caliper increase is measured by the laser caliper gauge. Data acquisition is started when the fluid flow is initiated specifically when the valve 714 is opened for the first time, and continues for 21 minutes or until the reservoir runs dry so that the 5 cm hydrohead is no longer maintained. The duration of one measurement is 21 min, laser caliper and balance readings are recorded regularly with an interval that may vary according to the measurement scope from 2 to 10 sec, and 3 replicates are measured.

After 21 min, the measurement of the 1$^{st}$ replicate is successfully completed and the controlled valve 714 closes automatically. The piston/cylinder assembly 713 is removed and the measurements of the 2$^{nd}$ and 3$^{rd}$ replicates are done accordingly, always following the same procedure. At the end of the measurement of the 3$^{rd}$ replicate, the controlled valve 714 stops the flow of liquid and stopcock 722 of the reservoir 708 is closed. The collected raw data is stored in the form of a simple data table, which then can be imported easily to a program for further analysis e.g. Excel 2003, SP3.

In the data table the following relevant information is reported for each reading:

Time from the beginning of the experiment

Weight of the liquid collected by the receiving vessel 707 on the balance 704

Caliper of the sample 718

The data from 30 seconds to the end of the experiment are used in the K(t) and uptake kinetics calculation. The data collected in the first 30 seconds are not included in the calculation. The effective permeability K(t) and the uptake kinetics of the absorbent structure are then determined using the equation sets below.

Used Equations:

The table below describes the notation used in the equations.

| | |
|---|---|
| A | x-section of the absorbent structure sample which corresponds to the cylinder inner radius: 28.27 cm$^2$ |
| h | height of water column, 5.0 cm |
| Δp | driving pressure applied by the 5.00 cm hydrohead (h): 4929.31 g/(cm s$^2$) |
| G | gravity constant: 981 cm/s$^2$ |
| η | Temperature dependent effective viscosity of the liquid in g/(cm s) |
| T | Temperature in ° C. |
| ρ | density of the liquid: 1.0053 g/cm$^3$ |
| $\rho_s^A$ | Apparent sample density of the porous medium or powder in g/cm$^3$ |
| $\rho_s$ | Average density of the solid part of the dry sample in g/cm$^3$ |
| $\rho_{s\,k}$ | Density of the component k of the dry sample in g/cm$^3$ |
| M | dry mass of the sample in g: 2.00 g if measuring superabsorbent particles |
| $m_k$ | Mass of the component k of the dry sample in g |
| $V_s$ | Dry sample volume in cm$^3$ |
| $t_i$ | time at step i of N discrete points in s |
| $d_i$ | caliper of the absorbent structure sample at time $t_i$ in cm |
| $r_i$ | reading of caliper instrument at time $t_i$ in cm |
| $r_r$ | reference reading of caliper instrument (reading of the piston/cylinder assembly without sample) in cm |
| $m_{out\,i}$ | balance reading at time $t_i$; mass of the liquid that left the sample at time $t_i$ in g |
| $U(t_i)$ | Sample uptake at time $t_i$ in g |
| T20 | time required to reach an uptake of 20 g/g, starting at 0 s ($t_0$) in s |
| U20 | Sample uptake after 20 minutes in g/g |
| T80% | Time required to reach an uptake of 80% of U20 starting at 0 s ($t_0$) in s |
| K20 | Sample permeability at 20 minutes in m$^2$ |
| Kmin | the minimum value of the permeability during the experiment in m$^2$ |
| Kmin/K20 | the ratio of Kmin and K20 |

The driving pressure is calculated from the hydro head as follows:

$$\Delta p = h \cdot G \cdot \rho = 4929.31 \text{ g/(cm·s}^2)$$

The caliper at each time $t_i$ is calculated as the difference of the caliper sensor reading at time $t_i$ and the reference reading without sample:

$$d_i = r_i - r_r \text{ [cm]}$$

For superabsorbent particles samples the caliper of the sample at time $t_i=0$ ($d_0$) is used to evaluate the quality of the particle sprinkling An apparent sample density inside the cylinder can be in fact calculated as:

$$\rho_s^A = \frac{m}{d_0 \cdot A} \ [g/cm^3]$$

If this apparent density inside the cylinder differs from the apparent density of the powder by more than ±40% the measurement has to be considered invalid and eliminated.

The apparent density can be measured according EDANA method 406.2-02 ("Superabsorbent materials-Polyacrylate superabsorbent powders-GRAVIMETRIC DETERMINATION OF DENSITY")

The rate of change with time of the balance reading at time $t_i$ is calculated as follows:

$$\frac{dm_{out}(t_i)}{dt} = \frac{m_{out_{i+1}} - m_{out_{i-1}}}{t_{i+1} - t_{i-1}} \ [g/sec]$$

The rate of change with time of the caliper reading at time $t_i$ is calculated as follows:

$$\frac{dd(t_i)}{dt} = \frac{d_{i+1} - d_{i-1}}{t_{i+1} - t_{i-1}} \ [cm/sec]$$

The uptake Kinetics is calculated as follows:

$$U(t_i) = \frac{(A \cdot d_i - V_s) \cdot \rho}{m} \ [g/g]$$

By dry sample volume ($V_s$) is intended the skeletal volume of the sample therefore $V_s$ is the actual volume occupied by the solid material in the dry sample excluding pores and interstitials that might be present.

$V_s$ can be calculated or measured by different methods known by the skilled person for example, knowing the exact composition and the skeletal density of the components it can be determined as follows:

$$V_S = \sum_k V_k = \sum_k \frac{m_k}{\rho_{Sk}} \ [cm^3]$$

Alternatively for an unknown material composition $V_s$ can be easily calculated as follow:

$$V_S = \frac{m}{\rho_S} \ [cm^3]$$

The average density $\rho_s$ can be determined by pycnometry with a suitable non-swelling liquid of known density. This technique cannot be performed on the same samples subsequently used for the K(t) measure therefore a suitable additional representative set of samples should be prepared for this experiment measurement.

From U(t) at the different time steps calculated as explained above, one can determine the uptake at any specific time by linear interpolation. For example one of the important outputs is the uptake at 20 minutes also called U20 (in g/g).

From U(t) at the different time steps one can also determine the time required to reach a certain uptake by linear interpolation. The time where the uptake of 20 g/g is first reached is called T20. Similarly the time to reach any other uptakes can be calculated accordingly (eg T5 or T10). Knowing U20 it is possible to determine from U(t) at the different time steps also the time to reach 80% of U20, this property is called T80%.

The Effective Permeability is calculated as follows from the rates of mass change and caliper change:

$$K(t_i) = \eta \frac{d_i}{\Delta p} \cdot \left( \frac{1}{\rho \cdot A} \cdot \frac{dm_{out}(t_i)}{dt} + \frac{dd(t_i)}{dt} \right) \ [cm^2]$$

The effective viscosity of the liquid depends on the temperature and in the interval of the experiment (23° C.±1° C.) is calculated according the following empirical equation:

$$\eta = -2.36 \cdot 10^{-4} \cdot T + 1.479 \cdot 10^{-2} \ [g/(cm \ s)]$$

From $K(t_i)$ one can determine the effective permeability at a certain time by linear interpolation. For example one of the important outputs is the uptake at 20 minutes or K20 ($m^2$). Similarly the Permeability at any other time can be calculated accordingly (e.g. K5 or K10).

Another parameter to be derived from the data is Kmin, which is the minimum K(t) value measured over the whole curve in the interval from $t_i$=30 s to $t_i$=1200 s. This value is useful to calculate Kmin/K20 which is the ratio between the minimum effective permeability and the permeability at 20 minutes. This parameter express the temporary gel blocking that might occur in some of the samples. If the value is close to 1 there is no temporary gel blocking if the value is close to 0 it is an indication that the material goes through a strong effective permeability drop when initially loaded with liquid.

The average values for T20, T80%, K20, U20 and Kmin/K20 are reported from 3 replicates according to the accuracy required as known by the skilled man.

Caliper Measurement Test Method

The intent of this method is to provide a procedure to determine the thickness of the absorbent core at the crotch point of an absorbent article. The test can be executed with a conventional caliper gauge, such as Type EG-225 available from ONO SOKKI Technology Inc., 2171 Executive Drive, Suite 400, Addison, Ill. 60101, USA, with an appropriate gauge stand, having an aluminium circular sample foot of 41 mm diameter, having a force exerted by the foot of 10 gf. An additional weight is added to achieve a total of 160 gf to adjust the pressure to 1.18 kPa (0.173 psi).

The thickness of the absorbent core is determined prior to assembly of the absorbent core in the absorbent article after the exact position which the absorbent core will have in the absorbent article upon assembly has been decided on. However, the thickness may also be determined after removing of the absorbent core from a finished product by any suitable method known by the person skilled in the art.

The crotch point of an absorbent article is determined at the intersection of the longitudinal centerline and the transverse centerline of the article.

Basic Protocol

1. All testing is conducted at 23±1° C. and 50±2% relative humidity.
2. The absorbent core is allowed to equilibrate at 23±1° C. and 50±2% relative humidity for 8 hours.
3. The crotch point is determined as described above and marked on the wearer surface of the absorbent core.
4. The absorbent core is positioned under the caliper gauge with the wearer surface toward the sample contact foot and with the crotch point centered under the foot.

5. The sample contact foot is gently lowered into contact with the surface of the absorbent core.
6. The caliper reading is taken 5 seconds after the foot comes into contact with the absorbent core.

Urine Permeability Measurement (UPM) Test Method
Urine Permeability Measurement System This method determined the permeability of a swollen hydrogel layer 1318. The equipment used for this method is described below. This method is closely related to the SFC (Salt Flow Conductivity) Test Method of the prior art.

Figure 10:
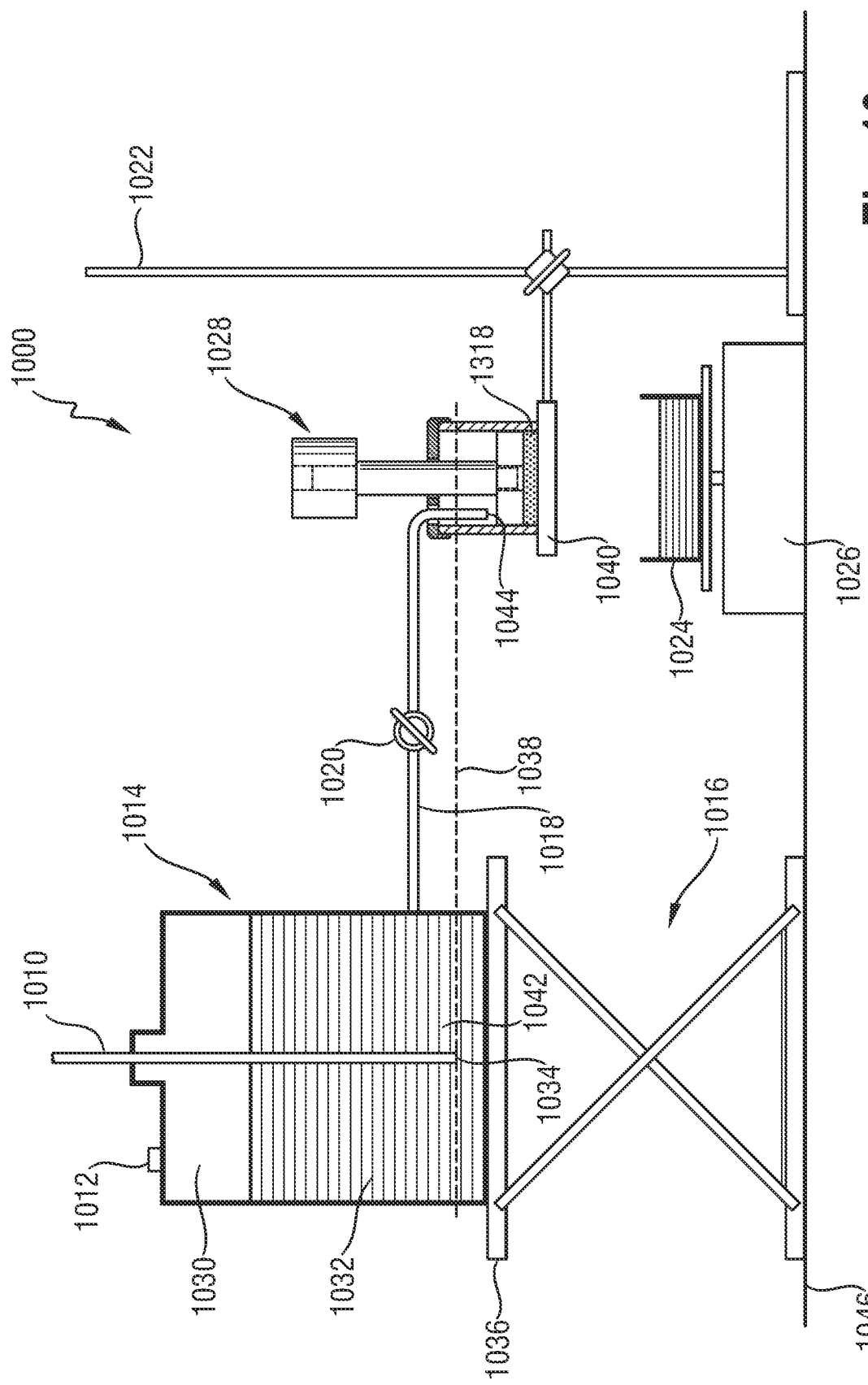
FIG. 10 is a partial cross-sectional side view of a suitable permeability measurement system for conducting the Urine Permeability Measurement Test.

FIG. 10 shows permeability measurement system 1000 set-up with the constant hydrostatic head reservoir 1014, open-ended tube for air admittance 1010, stoppered vent for refilling 1012, laboratory jack 1016, delivery tube 1018, stopcock 1020, ring stand support 1022, receiving vessel 1024, balance 1026 and piston/cylinder assembly 1028.

Figure 11:
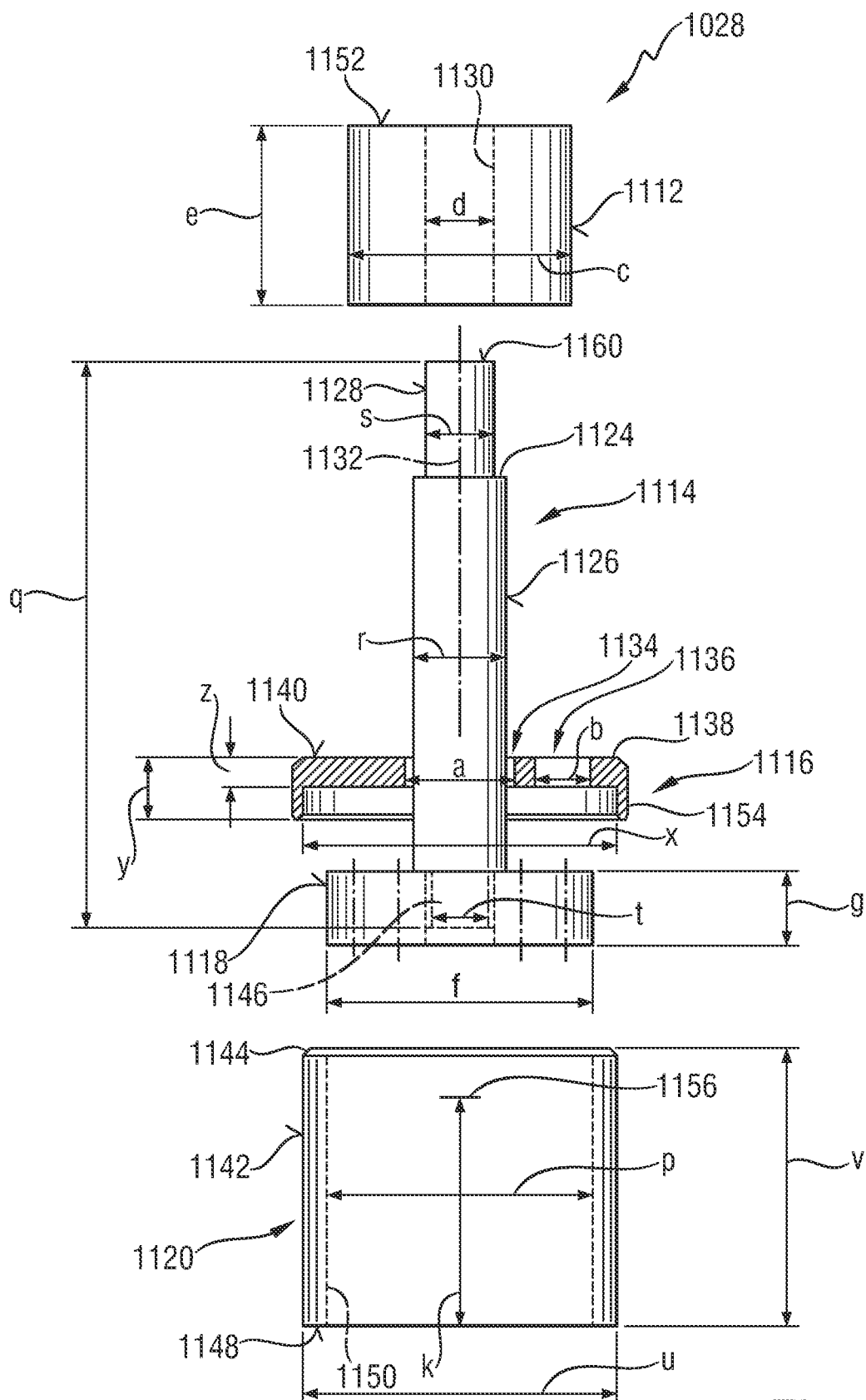
FIG. 11 is a cross-sectional side view of a piston/cylinder assembly for use in conducting the Urine Permeability Measurement Test.
Figure 12:
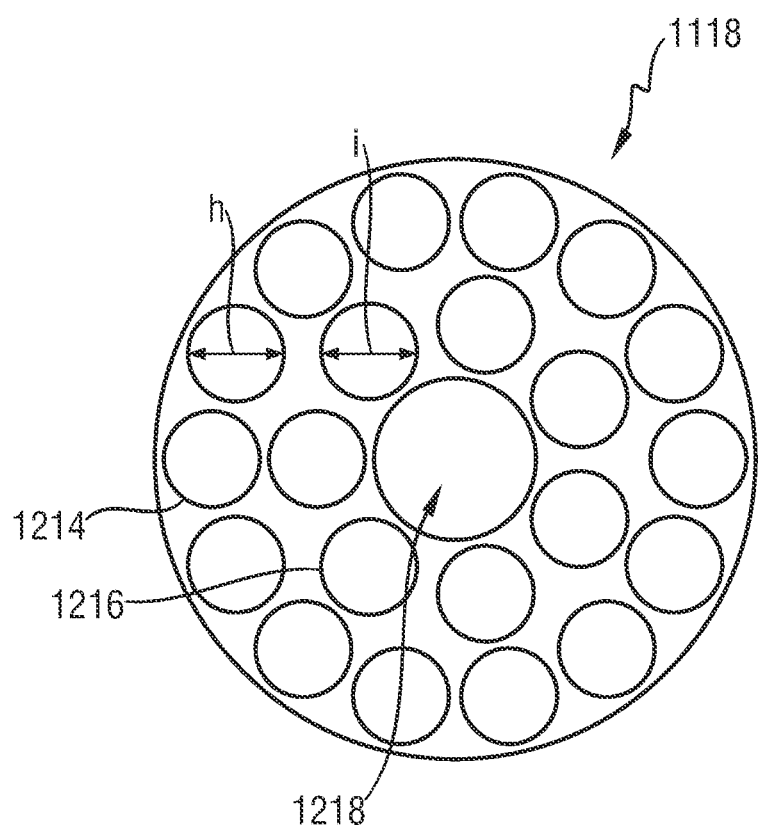
FIG. 12 is a top view of a piston head suitable for use in the piston/cylinder assembly shown in FIG. 11.

FIG. 11 shows the piston/cylinder assembly 1028 comprising a metal weight 1112, piston shaft 1114, piston head 1118, lid 1116, and cylinder 1120. The cylinder 1120 is made of transparent polycarbonate (e.g., Lexan®) and has an inner diameter p of 6.00 cm (area=28.27 cm$^2$) with inner cylinder walls 1150 which are smooth. The bottom 1148 of the cylinder 1120 is faced with a US. Standard 400 mesh stainless-steel screen cloth (not shown) that is bi-axially stretched to tautness prior to attachment to the bottom 1148 of the cylinder 1120. The piston shaft 1114 is made of transparent polycarbonate (e.g., Lexan®) and has an overall length q of approximately 127 mm. A middle portion 1126 of the piston shaft 1114 has a diameter r of 21.15 mm. An upper portion 1128 of the piston shaft 1114 has a diameter s of 15.8 mm, forming a shoulder 1124. A lower portion 1146 of the piston shaft 1114 has a diameter t of approximately ⅝ inch and is threaded to screw firmly into the center hole 1218 (see FIG. 12) of the piston head 1118. The piston head 1118 is perforated, made of transparent polycarbonate (e.g., Lexan®), and is also screened with a stretched US. Standard 400 mesh stainless-steel screen cloth (not shown). The weight 1112 is stainless steel, has a center bore 1130, slides onto the upper portion 1128 of piston shaft 1114 and rests on the shoulder 1124. The combined weight of the piston head 1118, piston shaft 1114 and weight 1112 is 596 g (±6 g), which corresponds to 0.30 psi over the area of the cylinder 1120. The combined weight may be adjusted by drilling a blind hole down a central axis 1132 of the piston shaft 1114 to remove material and/or provide a cavity to add weight. The cylinder lid 1116 has a first lid opening 1134 in its center for vertically aligning the piston shaft 1114 and a second lid opening 1136 near the edge 1138 for introducing fluid from the constant hydrostatic head reservoir 1014 into the cylinder 1120.

A first linear index mark (not shown) is scribed radially along the upper surface 1152 of the weight 1112, the first linear index mark being transverse to the central axis 1132 of the piston shaft 1114. A corresponding second linear index mark (not shown) is scribed radially along the top surface 1160 of the piston shaft 1114, the second linear index mark being transverse to the central axis 1132 of the piston shaft 1114. A corresponding third linear index mark (not shown) is scribed along the middle portion 1126 of the piston shaft 1114, the third linear index mark being parallel with the central axis 1132 of the piston shaft 1114. A corresponding fourth linear index mark (not shown) is scribed radially along the upper surface 1140 of the cylinder lid 1116, the fourth linear index mark being transverse to the central axis 1132 of the piston shaft 1114. Further, a corresponding fifth linear index mark (not shown) is scribed along a lip 1154 of the cylinder lid 1116, the fifth linear index mark being parallel with the central axis 1132 of the piston shaft 1114. A corresponding sixth linear index mark (not shown) is scribed along the outer cylinder wall 1142, the sixth linear index mark being parallel with the central axis 1132 of the piston shaft 1114. Alignment of the first, second, third, fourth, fifth, and sixth linear index marks allows for the weight 1112, piston shaft 1114, cylinder lid 1116, and cylinder 1120 to be re-positioned with the same orientation relative to one another for each measurement.

The cylinder 1120 specification details are:
Outer diameter u of the Cylinder 1120: 70.35 mm
Inner diameter p of the Cylinder 1120: 60.0 mm
Height v of the Cylinder 1120: 60.5 mm
The cylinder lid 1116 specification details are:
Outer diameter w of cylinder lid 1116: 76.05 mm
Inner diameter x of cylinder lid 1116: 70.5 mm
Thickness y of cylinder lid 1116 including lip 1154: 12.7 mm
Thickness z of cylinder lid 1116 without lip 1154: 6.35 mm
Diameter a of first lid opening 1134: 22.25 mm
Diameter b of second lid opening 1136: 12.7 mm
Distance between centers of first and second lid openings 1134 and 1136: 23.5 mm
The weight 1112 specification details are:
Outer diameter c: 50.0 mm
Diameter d of center bore 1130: 16.0 mm
Height e: 39.0 mm
The piston head 1118 specification details are
Diameter f: 59.7 mm
Height g: 16.5 mm
Outer holes 1214 (14 total) with a 9.65 mm diameter h, outer holes 1214 equally spaced with centers being 47.8 mm from the center of center hole 1218
Inner holes 1216 (7 total) with a 9.65 mm diameter i, inner holes 1216 equally spaced with centers being 26.7 mm from the center of center hole 1218
Center hole 1218 has a diameter j of ⅝ inches and is threaded to accept a lower portion 1146 of piston shaft 1114.

Prior to use, the stainless steel screens (not shown) of the piston head 1118 and cylinder 1120 should be inspected for clogging, holes or over-stretching and replaced when necessary. A urine permeability measurement apparatus with damaged screen can deliver erroneous UPM results, and must not be used until the screen has been replaced.

A 5.00 cm mark 1156 is scribed on the cylinder 1120 at a height k of 5.00 cm (±0.05 cm) above the screen (not shown) attached to the bottom 1148 of the cylinder 1120. This marks the fluid level to be maintained during the analysis. Maintenance of correct and constant fluid level (hydrostatic pressure) is critical for measurement accuracy.

A constant hydrostatic head reservoir 1014 is used to deliver salt solution 1032 to the cylinder 1120 and to maintain the level of salt solution 1032 at a height k of 5.00 cm above the screen (not shown) attached to the bottom 1148 of the cylinder 1120. The bottom 1034 of the air-intake tube 1010 is positioned so as to maintain the salt solution 1032 level in the cylinder 1120 at the required 5.00 cm height k during the measurement, i.e., bottom 1034 of the air tube 1010 is in approximately same plane 1038 as the 5.00 cm mark 1156 on the cylinder 1120 as it sits on the support screen (not shown) on the ring stand 1040 above the receiving vessel 1024. Proper height alignment of the air-intake tube 1010 and the 5.00 cm mark 1156 on the cylinder 1120 is critical to the analysis. A suitable reservoir 1014 consists of a jar 1030 containing: a horizontally oriented L-shaped delivery tube 1018 for fluid delivery, a vertically oriented open-ended tube 1010 for admitting air at a fixed height within the constant hydrostatic head reservoir 1014, and a stoppered vent 1012 for re-filling the constant hydrostatic head reservoir 1014. Tube 1010 has an internal diameter of 12.5 mm±0.5 mm. The delivery tube 1018, positioned near the bottom 1042 of the constant hydrostatic head reservoir 1014, contains a stopcock 1020 for starting/stopping the delivery of salt solution 1032. The outlet 1044 of the delivery tube 1018 is dimensioned to be inserted through the second lid opening 1136 in the cylinder lid 1116, with its end positioned below the surface of the salt solution 1032 in the cylinder 1120 (after the 5.00 cm height of the salt solution 1032 is attained in the cylinder 1120). The air-intake tube 1010 is held in place with an o-ring collar (not shown). The constant hydrostatic head reservoir 1014 can be positioned on a laboratory jack 1016 in order to adjust its height relative to that of the cylinder 1120. The components of the constant hydrostatic head reservoir 1014 are sized so as to rapidly fill the cylinder 1120 to the required height (i.e., hydrostatic head) and maintain this height for the duration of the measurement. The constant hydrostatic head reservoir 1014 must be capable of delivering salt solution 1032 at a flow rate of at least 3 g/sec for at least 10 minutes.

The piston/cylinder assembly 1028 is positioned on a 16 mesh rigid stainless steel support screen (not shown) (or equivalent) which is supported on a ring stand 1040 or suitable alternative rigid stand. This support screen (not shown) is sufficiently permeable so as to not impede salt solution 1032 flow and rigid enough to support the stainless steel mesh cloth (not shown) preventing stretching. The support screen (not shown) should be flat and level to avoid tilting the piston/cylinder assembly 1028 during the test. The salt solution 1032 passing through the support screen (not shown) is collected in a receiving vessel 1024, positioned below (but not supporting) the support screen (not shown). The receiving vessel 1024 is positioned on the balance 1026 which is accurate to at least 0.01 g. The digital output of the balance 1026 is connected to a computerized data acquisition system (not shown).

Preparation of Reagents (Not Illustrated)

Figure 13:
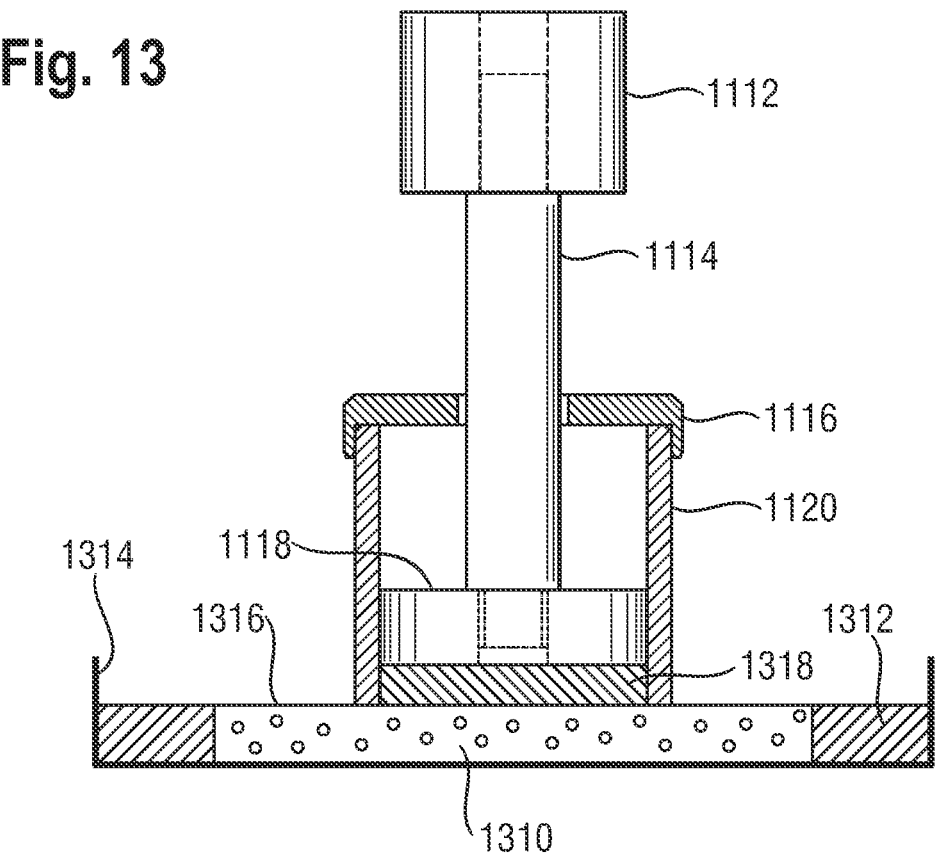
FIG. 13 is a cross-sectional side view of the piston/cylinder assembly of FIG. 11 placed on fitted disc for the swelling phase.

Jayco Synthetic Urine (JSU) 1312 (see FIG. 13) is used for a swelling phase (see UPM Procedure below) and 0.118 M Sodium Chloride (NaCl) Solution is used for a flow phase (see UPM Procedure below). The following preparations are referred to a standard 1 liter volume. For preparation of volumes other than 1 liter, all quantities are scaled accordingly.

JSU: A 1 L volumetric flask is filled with distilled water to 80% of its volume, and a magnetic stir bar is placed in the flask. Separately, using a weighing paper or beaker the following amounts of dry ingredients are weighed to within ±0.01 g using an analytical balance and are added quantitatively to the volumetric flask in the same order as listed below. The solution is stirred on a suitable stir plate until all the solids are dissolved, the stir bar is removed, and the solution diluted to 1 L volume with distilled water. A stir bar is again inserted, and the solution stirred on a stirring plate for a few minutes more.

Quantities of salts to make 1 liter of Jayco Synthetic Urine:
Potassium Chloride (KCl) 2.00 g
Sodium Sulfate ($Na_2SO_4$) 2.00 g
Ammonium dihydrogen phosphate ($NH_4H_2PO_4$) 0.85 g
Ammonium phosphate, dibasic (($NH_4$)$_2HPO_4$) 0.15 g
Calcium Chloride ($CaCl_2$) 0.19 g-[or hydrated calcium chloride ($CaCl_2 \cdot 2H_2O$) 0.25 g]
Magnesium chloride ($MgCl_2$) 0.23 g-[or hydrated magnesium chloride ($MgCl_2 \cdot 6H_2O$) 0.50 g]

To make the preparation faster, each salt is completely dissolved before adding the next one. Jayco synthetic urine may be stored in a clean glass container for 2 weeks. The solution should not be used if it becomes cloudy. Shelf life in a clean plastic container is 10 days.

0.118 M Sodium Chloride (NaCl) Solution: 0.118 M Sodium Chloride is used as salt solution 1032. Using a weighing paper or beaker 6.90 g (±0.01 g) of sodium chloride is weighed and quantitatively transferred into a 1 L volumetric flask; and the flask is filled to volume with distilled water. A stir bar is added and the solution is mixed on a stirring plate until all the solids are dissolved.

Test Preparation

Using a solid reference cylinder weight (not shown) (40 mm diameter; 140 mm height), a caliper gauge (not shown) (e.g., Mitotoyo Digimatic Height Gage) is set to read zero. This operation is conveniently performed on a smooth and level bench top 1046. The piston/cylinder assembly 1028 without superabsorbent polymer particles is positioned under the caliper gauge (not shown) and a reading, $L_1$, is recorded to the nearest 0.01 mm.

The constant hydrostatic head reservoir 1014 is filled with salt solution 1032. The bottom 1034 of the air-intake tube 1010 is positioned so as to maintain the top part (not shown) of the liquid meniscus (not shown) in the cylinder 1120 at the 5.00 cm mark 1156 during the measurement. Proper height alignment of the air-intake tube 1010 at the 5.00 cm mark 1156 on the cylinder 1120 is critical to the analysis.

The receiving vessel 1024 is placed on the balance 1026 and the digital output of the balance 1026 is connected to a computerized data acquisition system (not shown). The ring stand 1040 with a 16 mesh rigid stainless steel support screen (not shown) is positioned above the receiving vessel 1024. The 16 mesh screen (not shown) should be sufficiently rigid to support the piston/cylinder assembly 1028 during the measurement. The support screen (not shown) must be flat and level.

UPM Procedure 1.5 g (±0.05 g) of superabsorbent polymer particles is weighed onto a suitable weighing paper or weighing aid using an analytical balance. The moisture content of the superabsorbent polymer particles is measured according to the Edana Moisture Content Test Method 430.1-99 ("Superabsorbent materials-Polyacrylate superabsorbent powders-Moisture Content-weight loss upon heating" (February 99)). If the moisture content of the superabsorbent polymer particles is greater than 5%, then the superabsorbent polymer particles weight should be corrected for moisture (i.e., in that particular case the added superabsorbent polymer particles should be 1.5 g on a dry-weight basis).

The empty cylinder 1120 is placed on a level benchtop 1046 and the superabsorbent polymer particles are quantitatively transferred into the cylinder 1120. The superabsorbent polymer particles are evenly dispersed on the screen (not shown) attached to the bottom 1148 of the cylinder 1120 by gently shaking, rotating, and/or tapping the cylinder 1120. It is important to have an even distribution of particles on the screen (not shown) attached to the bottom 1148 of the cylinder 1120 to obtain the highest precision result. After the superabsorbent polymer particles have been evenly distributed on the screen (not shown) attached to the bottom 1148 of the cylinder 1120 particles must not adhere to the inner cylinder walls 1150. The piston shaft 1114 is inserted through the first lid opening 1134, with the lip 1154 of the lid 1116 facing towards the piston head 1118. The piston head 1118 is carefully inserted into the cylinder 1120 to a depth of a few centimeters. The lid 1116 is then placed onto the upper rim 1144 of the cylinder 1120 while taking care to keep the piston head 1118 away from the superabsorbent polymer particles. The lid 1116 and piston shaft 1126 are then carefully rotated so as to align the third, fourth, fifth, and sixth linear index marks are then aligned. The piston head 1118 (via the piston shaft 1114) is then gently lowered to rest on the dry superabsorbent polymer particles. The weight 1112 is positioned on the upper portion 1128 of the piston shaft 1114 so that it rests on the shoulder 1124 such that the first and second linear index marks are aligned. Proper seating of the lid 1116 prevents binding and assures an even distribution of the weight on the hydrogel layer 1318.

Swelling Phase: An 8 cm diameter fritted disc (7 mm thick; e.g. Chemglass Inc. #CG 201-51, coarse porosity) 1310 is saturated by adding excess JSU 1312 to the fitted disc 1310 until the fritted disc 1310 is saturated. The saturated fitted disc 1310 is placed in a wide flat-bottomed Petri dish 1314 and JSU 1312 is added until it reaches the top surface 1316 of the fitted disc 1310. The JSU height must not exceed the height of the fitted disc 1310.

The screen (not shown) attached to the bottom 1148 of the cylinder 1120 is easily stretched. To prevent stretching, a sideways pressure is applied on the piston shaft 1114, just above the lid 1116, with the index finger while grasping the cylinder 1120 of the piston/cylinder assembly 1028. This "locks" the piston shaft 1114 in place against the lid 1116 so that the piston/cylinder assembly 1028 can be lifted without undue force being exerted on the screen (not shown).

The entire piston/cylinder assembly 1028 is lifted in this fashion and placed on the fitted disc 1310 in the Petri dish 1314. JSU 1312 from the Petri dish 1314 passes through the fritted disc 1310 and is absorbed by the superabsorbent polymer particles (not shown) to form a hydrogel layer 1318. The JSU 1312 available in the Petri dish 1314 should be enough for all the swelling phase. If needed, more JSU 1312 may be added to the Petri dish 1314 during the hydration period to keep the JSU 1312 level at the top surface 1316 of the fitted disc 1310. After a period of 60 minutes, the piston/cylinder assembly 1028 is removed from the fitted disc 1310, taking care to lock the piston shaft 1114 against the lid 1116 as described above and ensure the hydrogel layer 1318 does not lose JSU 1312 or take in air during this procedure. The piston/cylinder assembly 1028 is placed under the caliper gauge (not shown) and a reading, $L_2$, is recorded to the nearest 0.01 mm. If the reading changes with time, only the initial value is recorded. The thickness of the hydrogel layer 1318, $L_0$ is determined from $L_2-L_1$ to the nearest 0.1 mm.

The piston/cylinder assembly 1028 is transferred to the support screen (not shown) attached to the ring support stand 1040 taking care to lock the piston shaft 1114 in place against the lid 1116. The constant hydrostatic head reservoir 1014 is positioned such that the delivery tube 1018 is placed through the second lid opening 1136. The measurement is initiated in the following sequence:
a) The stopcock 1020 of the constant hydrostatic head reservoir 1014 is opened to permit the salt solution 1032 to reach the 5.00 cm mark 1156 on the cylinder 1120. This salt solution 1032 level should be obtained within 10 seconds of opening the stopcock 1020.
b) Once 5.00 cm of salt solution 1032 is attained, the data collection program is initiated.

With the aid of a computer (not shown) attached to the balance 1026, the quantity of salt solution 1032 passing through the hydrogel layer 1318 is recorded at intervals of 20 seconds for a time period of 10 minutes. At the end of 10 minutes, the stopcock 1020 on the constant hydrostatic head reservoir 1014 is closed.

The data from 60 seconds to the end of the experiment are used in the UPM calculation. The data collected prior to 60 seconds are not included in the calculation. The flow rate $F_s$ (in g/s) is the slope of a linear least-squares fit to a graph of the weight of salt solution 1032 collected (in grams) as a function of time (in seconds) from 60 seconds to 600 seconds.

The Urine Permeability Measurement (Q) of the hydrogel layer 1318 is calculated using the following equation:

$$Q=[F_g \times L_0]/[\rho \times A \times \Delta P],$$

where $F_g$ is the flow rate in g/sec determined from regression analysis of the flow rate results, $L_0$ is the initial thickness of the hydrogel layer 1318 in cm, $\rho$ is the density of the salt solution 1032 in gm/cm$^3$. A (from the equation above) is the area of the hydrogel layer 1318 in cm$^2$, $\Delta P$ is the hydrostatic pressure in dyne/cm$^2$, and the Urine Permeability Measurement, Q, is in units of cm$^3$ sec/gm. The average of three determinations should be reported.

FSR Test Method

This method determines the speed of superabsorbent polymer particles, especially polymeric hydrogelling particles, such as cross-linked poly-acrylates to swell in 0.9% Saline (aqueous 0.9 mass % NaCl solution). The measurement principle is to allow superabsorbent polymer particles to absorb a known amount of fluid, and the time taken to absorb the fluid is measured. The result is then expressed in grams of absorbed fluid per gram of material per second. All testing is conducted at 23±2° C.

Four grams of a representative sample of the superabsorbent polymer particles is dried in an uncovered 5 cm diameter Petri dish in a vacuum chamber at 23±2° C. and 0.01 torr or lower for 48 hours prior to measurement.

About 1 g (+/−0.1 g) of the test specimen is removed from the vacuum chamber and immediately weighed to an accuracy of 0.001 g into a 25 ml beaker, which has 32 to 34 mm inside diameter, and 50 mm height. The material is evenly spread over the bottom. 20 g of 0.9% Saline are weighed to an accuracy of +/−0.01 g in a 50 ml beaker, and are then poured carefully but quickly into the beaker containing the test material. A timer is started immediately upon the liquid contacting the material. The beaker is not moved or agitated during swelling.

The timer is stopped, and the time recorded to the nearest second (or more accurately if appropriate), when the last part of undisturbed fluid is reached by the swelling particles. In order to increase the reproducibility of the determination of the end point, the liquid surface can be illuminated by a small lamp without heating the surface by that lamp. The beaker is re-weighed to determine the actually picked up liquid to within ±0.1 g.

The free-swell rate is calculated by dividing the weight of superabsorbent polymer particles by the amount of actually picked up liquid, and dividing the result by the time required for this pick up, and is expressed in "g/g/s". Three measurements are performed and the results averaged to obtain the FSR value in g/g/s, reported to 3 significant figures.

Flat Acquisition Test Method

This method determines the acquisition times of a baby diaper typically designated for wearers having a weight in the range of 8 to 13 kg±20% (such as Pampers Active Fit size 4 or other Pampers baby diapers size 4, Huggies baby diapers size 4 or baby diapers size 4 of most other tradenames).

Apparatus

Figure 14:
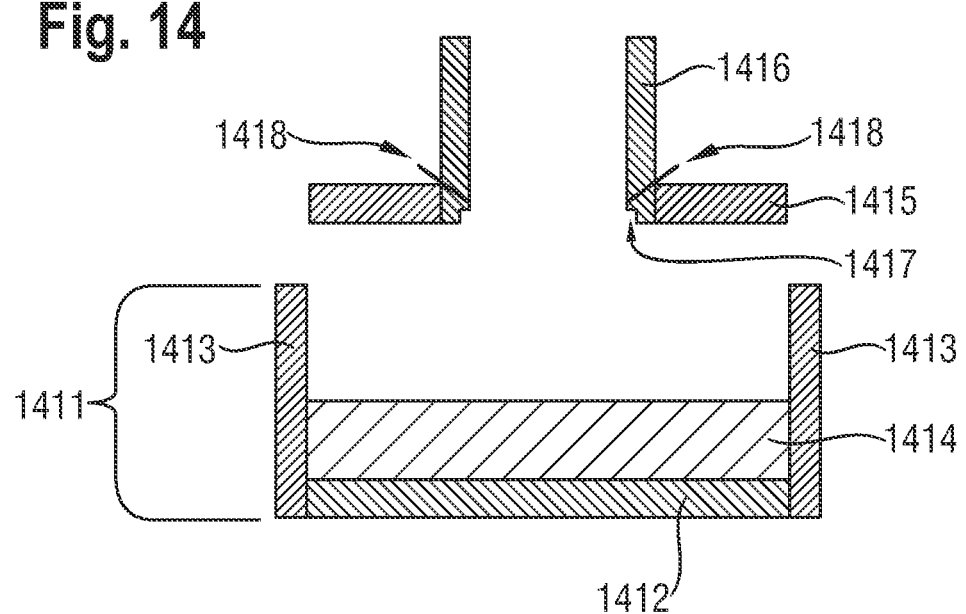
FIG. 14 is a cross-sectional view of a suitable Flat Acquisition measurement system for conducting the Flat Acquisition Test.

The test apparatus is shown in FIG. 14 and comprises a trough 1411 made of polycarbonate (e.g. Lexan®) nominally 12.5 mm (0.5 inch) in thickness. The trough 1411 comprises a rectilinear horizontal base 1412 having a length of 508 mm (20.0 inches), and a width of 152 mm (6.0 inches). Two rectilinear vertical sides 1413 64 mm (2.5 inches) tall×508 mm (20 inches) in length are affixed to the long edges of the base 1412 to form a U-shaped trough 1411 having a length of 508 mm (20.0 inches), an internal width of 152 mm (6.0 inches), and an internal depth of 51 mm (2.0 inches). The front and back ends of the trough 1411 are not enclosed.

A slab of open-cell polyurethane foam 1414 with dimensions 508×152×25 mm is wrapped in polyethylene film and placed in the bottom of the trough 1411 in such a way that the edges of the foam 1414 and the trough 1411 are aligned, and the upper surface of the polyethylene film is smooth and free of seams, wrinkles or imperfections. The polyurethane foam 1414 has a compressive modulus of 0.48 psi. A reference line is drawn across the width of the upper surface of the polyethylene cover 152 mm (6.0 inches) from one end (the front edge) parallel to the transverse centerline using an indelible marker.

A rectilinear polycarbonate top plate 1415 has a nominal thickness of 12.5 mm (0.5 inch), a length of 508 mm (20.0 inches), and a width of 146 mm (5.75 inches). A 51 mm (2.0 inch) diameter hole is bored in the center of the top plate 1415 (i.e. the center of the hole is located at the intersection of the longitudinal and transverse axes of the upper surface of the top plate 1415). A polycarbonate cylinder 1416 with an outside diameter of 51 mm (2.0 inches), an internal diameter of 37.5 mm (1.5 inches) and a height of 102 mm (4.0 inches) is glued into the hole in the top plate 1415 so that the bottom edge of the cylinder 1416 is flush with the lower surface of the top plate 1415 and the cylinder 1416 protrudes vertically 89 mm (3.5 inches) above the upper surface of the top plate 1415, and the seam between the cylinder 1416 and the top plate 1415 is watertight. An annular recess 1417 with a height of 2 mm and a diameter of 44.5 mm (1.75 inches) is machined into the bottom internal edge of the cylinder 1416. Two 1 mm diameter holes are drilled at a 45° angle to the upper surface of the top plate 1415 so that the holes intersect the inner surface of the cylinder 1416 immediately above the recess 1417 and are at opposite sides of the cylinder 1416 (i.e. 180° apart). Two stainless steel wires 1418 having a diameter of 1 mm are glued into the holes in a watertight fashion so that one end of each wire is flush with the inner cylinder wall and the other end protrudes from the upper surface of the top plate 1415. These wires are referred to as electrodes hereinbelow. A reference line is scribed across the width of the top plate 1415 152 mm (6.0 inches) from the front edge parallel to the transverse centerline. The top plate 1415/cylinder 1416 assembly has a weight of approximately 1180 grams.

Two steel weights each weighing 9.0 Kg and measuring 146 mm (5.75 inches) wide, 76 mm (3.0 inches) deep, and approximately 100 mm (4 inches tall) are also required.
Procedure:

All testing is carried out at 23±2° C. and 35±15% relative humidity.

The polycarbonate trough 1411 containing the wrapped foam slab 1414 is placed on a suitable flat horizontal surface. A disposable absorbent product is removed from its packaging and the cuff elastics are cut at suitable intervals to allow the product to lay flat. The product is weighed to within ±0.1 grams on a suitable top-loading balance then placed on the covered foam slab 1414 in the acquisition apparatus with the front waist edge of the product aligned with the reference mark on the polyethylene cover. The product is centered along the longitudinal centerline of the apparatus with the topsheet (body-side) of the product facing upwards and the rear waist edge toward the rear end of the foam slab 1414. The top plate 1415 is placed on top of the product with the protruding cylinder facing upwards. The scribed reference line is aligned with the front waist edge of the product and the rear end of the top plate 1415 is aligned with the rear edge of the foam slab 1414. The two 9.0 Kg weights are then gently placed onto the top plate 1415 so that the width of each weight is parallel to the transverse centerline of the top plate, and each weight is 83 mm (3.25 inches) from the front or rear edge of the top plate 1415.

A suitable electrical circuit is connected to the two electrodes to detect the presence of an electrically conductive fluid between them.

A suitable pump; e.g. Model 7520-00 supplied by Cole Parmer Instruments, Chicago, USA, or equivalent; is set up to discharge a 0.9 mass % aqueous solution of sodium chloride through a flexible plastic tube having an internal diameter of 4.8 mm (3/16 inch), e.g., Tygon® R-3603 or equivalent. The end portion of the tube is clamped vertically so that it is centered within the cylinder 1416 attached to the top plate 1415 with the discharge end of the tube facing downwards and located 50 mm (2 inches) below the upper edge of the cylinder 1416. The pump is operated via a timer and is pre-calibrated to discharge a gush of 75.0 ml of the 0.9% saline solution at a rate of 15 ml/sec.

The pump is activated and a timer started immediately upon activation. The pump delivers 75 mL of 0.9% NaCl solution to the cylinder 1416 at a rate of 15 ml/sec, then stops. As test fluid is introduced to the cylinder 1416, it typically builds up on top of the absorbent structure to some extent. This fluid completes an electrical circuit between the two electrodes in the cylinder. After the gush has been delivered, the meniscus of the solution drops as the fluid is absorbed into the structure. When the electrical circuit is broken due to the absence of free fluid between the electrodes in the cylinder, the time is noted.

The acquisition time for a particular gush is the time interval between activation of the pump for that gush, and the point at which the electrical circuit is broken.

Four gushes are delivered to the product in this fashion; each gush is 75 ml and is delivered at 15 ml/sec. The time interval between the beginning of each gush is 300 seconds.

The acquisition time for four gushes is recorded. Three products are tested in this fashion and the average gush time for each of the respective gushes (first through fourth) is calculated.

EXAMPLES

Superabsorbent polymer particles according to the present disclosure have been prepared to compare their properties with the properties of superabsorbent polymer particles of the prior art.

Comparative Example 1

The superabsorbent polymer particles of the comparative example are the superabsorbent polymer particles which are used in Pampers Active Fit diapers commercially available in the UK in August 2010. These superabsorbent polymer particles are generally made according to US 2009/0275470A1. It should be noted that the superabsorbent polymer particles may be isolated from the commercially available Pampers Active Fit diapers as described in European patent application no 10154618.2 entitled "Method of separating superabsorbent polymer particles from a solidified thermoplastic composition comprising polymers".

The Standard particle size distribution of the superabsorbent polymer particles is of 45 to 710 µm with a maximum of 1% below 45 µm and a maximum of 1% above 710 µm.

Comparative Example 2

300 g of superabsorbent polymer particles have been prepared according to comparative example 11 disclosed in the PCT patent application WO 2010/095427 A1 entitled "Polyacrylic acid-based water-absorbing resin powder and method for producing the same".

Example 1

4000 kg of superabsorbent polymer particles of the comparative example have been sieved over a AISI 304 standard 300 μm stainless steel wire mesh in a riddle sieve equipment with a capacity of about 100-150 kg per hours yielding to 750 kg of superabsorbent polymer particles with a medium diameter (D50) of about 180-200 μm and a particle size distribution of 45 to 300 μm with a maximum of 3% below 45 μm and a maximum of 3% above 300 μm.

Example 2

300 g of superabsorbent polymer particles have been prepared according to example 9 disclosed in the PCT patent application WO 2010/095427 A1 entitled "Polyacrylic acid-based water-absorbing resin powder and method for producing the same".

Several parameters of the superabsorbent polymer particles of Examples 1, 2, 3 and of the comparative example have been measured: the time to reach an uptake of 20 g/g (T20), the uptake at 20 min (U20), the time to reach an uptake of 80% of U20 (T80%), the effective permeability at 20 minutes (K20) and the transient gel blocking index (Kmin/K20) have been measured according to K(t) Test Method set out above. The UPM (Urine Permeability Measurement) has been measured according to the UPM Test Method set out above. The CRC (Centrifuge Retention Capacity) has been measured according to EDANA method WSP 241.2-05.

Figure 15A:
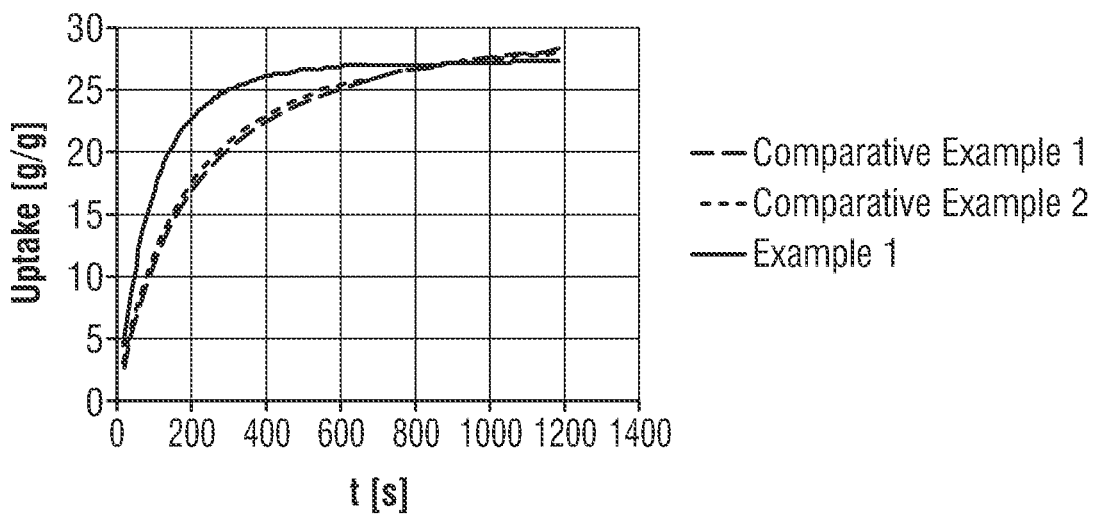
FIG. 15A is a graphic representing the uptake in g/g as a function of time for the comparative examples 1 and 2 and Example 1 as measured according to the K(t) Test Method.
Figure 15B:
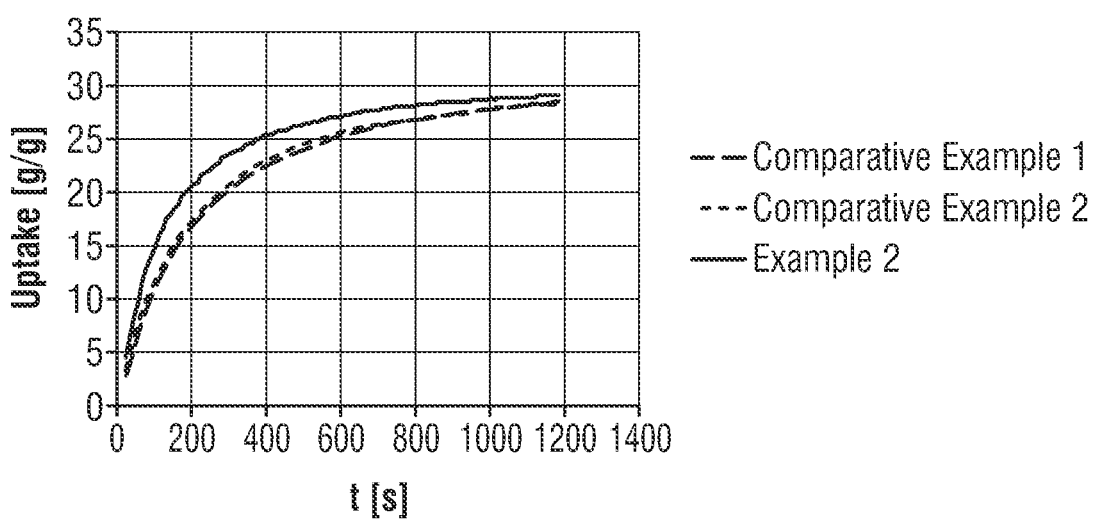
FIG. 15B is a graphic representing the uptake in g/g as a function of time for the comparative examples 1 and 2 and Example 2 as measured according to the K(t) Test Method

FIGS. 15A and 15B represent the uptake in g/g as a function of time for the Comparative examples 1 and 2 vs. Examples 1 and 2 as measured according to the K(t) Test Method set out above.

The different values for the measured parameters are summarized in Table 1 below.

TABLE 1

| Examples | T20(s) | U20 (g/g) | T80% (g/g) | K20 (cm$^2$) | Kmin/Kmax | UPM (1 × 10$^{-7}$ cm3 · s)/g) | CRC (g/g) |
|---|---|---|---|---|---|---|---|
| Comparative Example 1 | 291 ± 19 | 28.5 | 418 ± 20 | 8.8 · 10$^{-8}$ | 0.88 | 98 | 26.5 |
| Comparative Example 2 | 263 ± 1 | 29.2 | 402 ± 12 | 9.3 · 10$^{-8}$ | 1 | 110 | 27.3 |
| Example 1 | 138 ± 2 | 27.4 | 176 ± 1 | 3.5 · 10$^{-8}$ | 0.78 | 66 | 24.1 |
| Example 2 | 194 ± 5 | 30.2 | 330 ± 9 | 8.7 · 10$^{-8}$ | 0.8 | 100 | 27.7 |

As can be seen from FIGS. 15A and 15B and from Table 1, the times to reach an uptake of 20 g/g (T20) as measured according to the K(t) Test Method for superabsorbent polymer particles made according to examples 1 and 2 are significantly lower than for superabsorbent polymer particles made according to the comparative examples 1 and 2. Therefore, these superabsorbent polymer particles are able to rapidly absorb liquid even in the dry stage, i.e. upon initial exposure to liquid.

As can also be seen from Table 1 is that superabsorbent polymer particles having a high permeability at equilibrium (high UPM value) such as the superabsorbent polymer particles of comparative example 1 and 2 do not automatically have a high T20 value which means that the permeability at equilibrium is not a reliable criteria in order to select superabsorbent polymer particles which are able to rapidly absorb liquid upon initial exposure to liquid.

Acquisition times of diapers comprising superabsorbent polymer particles of comparative examples 1 or 2 vs. diapers comprising superabsorbent polymer particles according to the present disclosure.

Acquisition times of Pampers Active Fit size 4 diapers commercially available in the UK in August 2010 have been measured according to the Flat Acquisition Test Method set out above. These diapers comprise superabsorbent polymer particles of the comparative example 1. Acquisition times of the same diapers wherein the superabsorbent polymer particles have been replaced by the superabsorbent polymer particles of comparative example 2 or by the superabsorbent polymer particles of example 2 have been measured according to the Flat acquisition Test Method set out above. The absorbent cores of all the diapers have a dry thickness at the crotch point of the diaper of 1.7 mm as measured according to the Caliper Measurement Test Method set out above. The values obtained for the acquisition times of all samples are summarized in Table 2 below.

TABLE 2

| | Samples | | |
|---|---|---|---|
| | Comparative Example 1 | Comparative Example 2 | Example 2 |
| Acquisition time of 1st gush (75 mL) in s | 30 | 28 | 26 |

As can be seen from Table 2 above, the acquisition times of the first gush for diapers comprising superabsorbent polymer particles according to comparative examples 1 or 2 are higher than the acquisition time of the first gush for the same diaper wherein the superabsorbent polymer particles have been replaced by the superabsorbent polymer particles of Example 2.

Hence, absorbent articles according to the present disclosure, namely absorbent articles comprising superabsorbent polymer particles which require a time to reach an uptake of 20 g/g (T20) of less than 240, as measured according to the K(t) method set out below have improved absorption properties, especially at the first gush, i.e. when the article starts to be wetted.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising an absorbent core, the absorbent article being divided into three portions: a front portion, a back portion and a crotch portion disposed between the front portion and the back portion, the absorbent core having a dry thickness at a crotch point of the article of from 0.2 to 5 mm;
    wherein the absorbent core comprises at least 90% of superabsorbent polymer particles, and
    wherein the superabsorbent polymer particles comprised by the absorbent core in the front portion or the crotch portion of the absorbent article or by the whole absorbent core require a time to reach an uptake of 20 g/g (T20) of less than 240 s as measured according to the K(t) Test Method
    wherein the superabsorbent polymer particles comprised by the absorbent core in the front portion or the crotch portion of the absorbent article or by the whole absorbent core have an effective permeability at 20 minutes (K20) of at least $5*10-8$ cm2 as measured according to the K(t) Test Method.

2. The absorbent article according to claim 1, wherein the absorbent article comprises a topsheet and a backsheet and wherein the absorbent core is sandwiched between the topsheet and the backsheet.

3. The absorbent article according to claim 2, comprising an acquisition system, wherein the acquisition system is disposed between the topsheet and the absorbent core and does not comprise superabsorbent polymer particles.

4. The absorbent article according to claim 2, wherein the superabsorbent polymer particles are comprised in the absorbent core, such that the superabsorbent polymer particles are deposited between a first and a second substrate layer, with the first substrate layer facing towards the backsheet and the second substrate layer facing towards the topsheet.

5. The absorbent article according to claim 4, wherein the superabsorbent polymer particles are immobilized by thermoplastic adhesive material.

6. The absorbent article according to claim 5, wherein the thermoplastic adhesive material forms a fibrous network over the superabsorbent polymer particles.

7. The absorbent article according to claim 1, wherein the uptake of the superabsorbent polymer particles comprised by the absorbent core in the front portion or the crotch portion of the absorbent article or by the whole absorbent core at 20 min (U20) is of at least 28 g/g as measured according to the K(t) Test Method.

8. The absorbent article according to claim 7, wherein the absorbent article comprises a topsheet and a backsheet, and wherein the absorbent core is sandwiched between the topsheet and the backsheet.

9. The absorbent article according to claim 1, wherein the superabsorbent polymer particles have a UPM value of from 40 to 150 ($10^{-7}$ (cm$^3$·s)/g).

10. The absorbent article according to claim 1, wherein the superabsorbent polymer particles have a CRC value of from 20 to 40 g/g.

11. The absorbent article according to claim 1, wherein the superabsorbent polymer particles have a particle size of from 50 to 550 μm.

12. The absorbent article according to claim 1, wherein the absorbent core is airfelt free.

13. The absorbent article according to claim 1, wherein the absorbent core comprises an average amount of superabsorbent polymer particles per surface area of the absorbent core of from 200 to 900 g/m$^2$ in the crotch portion of the absorbent article.

14. The absorbent article according to claim 1, wherein the absorbent article has an acquisition time for the first gush of less than 27 s as measured according to the Flat Acquisition Test Method.

15. The absorbent article according to claim 1, wherein the absorbent core comprises a first substrate layer, at least a portion of the superabsorbent polymer particles being deposited on the first substrate layer and thermoplastic adhesive material immobilizing the superabsorbent polymer particles.

16. The absorbent article according to claim 15, wherein the absorbent core comprises a second substrate layer, at least a portion of the superabsorbent polymer particles being deposited on the second substrate layer and thermoplastic adhesive material immobilizing the superabsorbent polymer particles, the first and second substrate layers being combined together such that at least a portion of the thermoplastic adhesive material of the first substrate layer contacts at least a portion of the thermoplastic adhesive material of the second substrate layer.

* * * * *

UNITED STATES PATENT AND TRADEMARK OFFICE
CERTIFICATE OF CORRECTION

PATENT NO. : 8,921,641 B2
APPLICATION NO. : 13/524006
DATED : December 30, 2014
INVENTOR(S) : Bruno Johannes Ehrnsperger et al.

Page 1 of 1

It is certified that error appears in the above-identified patent and that said Letters Patent is hereby corrected as shown below:

In the Claims

Column 36, Line 22 (claim 11) - Change "…50 to 550μm." to --…50 to 850μm.--

Signed and Sealed this
Seventh Day of April, 2015

Michelle K. Lee
*Director of the United States Patent and Trademark Office*